United States Patent
Cha et al.

(10) Patent No.: US 12,004,421 B2
(45) Date of Patent: Jun. 4, 2024

(54) COMPOUND AND ORGANIC LIGHT EMITTING DEVICE COMPRISING THE SAME

(71) Applicant: LG CHEM, LTD., Seoul (KR)

(72) Inventors: Yongbum Cha, Daejeon (KR); Sung Kil Hong, Daejeon (KR); Dong Uk Heo, Daejeon (KR); Wanpyo Hong, Daejeon (KR); Sujeong Geum, Daejeon (KR)

(73) Assignee: LG CHEM, LTD., Seoul (KR)

( * ) Notice: Subject to any disclaimer, the term of this patent is extended or adjusted under 35 U.S.C. 154(b) by 673 days.

(21) Appl. No.: 17/260,763

(22) PCT Filed: Aug. 2, 2019

(86) PCT No.: PCT/KR2019/009675
§ 371 (c)(1),
(2) Date: Jan. 15, 2021

(87) PCT Pub. No.: WO2020/071627
PCT Pub. Date: Apr. 9, 2020

(65) Prior Publication Data
US 2021/0296593 A1    Sep. 23, 2021

(30) Foreign Application Priority Data

Oct. 2, 2018 (KR) .......... 10-2018-0117683
Jul. 31, 2019 (KR) .......... 10-2019-0093314

(51) Int. Cl.
*H10K 85/60* (2023.01)
*C07D 213/57* (2006.01)
(Continued)

(52) U.S. Cl.
CPC ......... *H10K 85/654* (2023.02); *C07D 213/57* (2013.01); *C07D 239/26* (2013.01);
(Continued)

(58) Field of Classification Search
CPC .......................... C07D 251/24; C07D 409/14
See application file for complete search history.

(56) References Cited

U.S. PATENT DOCUMENTS 9,882,146 B2 * 1/2018 Lee .............. C07D 405/14
2004/0251816 A1 12/2004 Leo et al.
(Continued)

FOREIGN PATENT DOCUMENTS

CN   104276997         1/2015
JP   2006225322 A  *  8/2006
(Continued)

OTHER PUBLICATIONS

Machine translation of JP 2006-225322 (no date).*
Machine translation of the PCT written opinion (ETWOS—no date).*

*Primary Examiner* — Amanda C. Walke
(74) *Attorney, Agent, or Firm* — BRYAN CAVE LEIGHTON PAISNER LLP

(57) ABSTRACT

Provided is a compound of Chemical Formula 1:

Chemical Formula 1

(Continued)

wherein, in Chemical Formula 1:
$X_1$ to $X_3$ are each independently N or CH, provided that at least one of $X_1$ to $X_3$ is N; $X_4$ to $X_6$ are each independently N or CH, provided that at least one of $X_4$ to $X_6$ is N; $Ar_1$ to $Ar_4$ are each independently a substituted or unsubstituted $C_{6-60}$ aryl, or a substituted or unsubstituted $C_{2-60}$ heteroaryl containing any one or more selected from the group consisting of N, O, and S; $L_1$ to $L_3$ are each independently a single bond, a substituted or unsubstituted $C_{6-60}$ arylene, or a substituted or unsubstituted $C_{2-60}$ heteroarylene containing any one or more selected from the group consisting of N, O, and S; and n is 1 or 2, and an organic light emitting device including the same.

15 Claims, 1 Drawing Sheet

(51) Int. Cl.
  *C07D 239/26* (2006.01)
  *C07D 251/24* (2006.01)
  *C07D 401/14* (2006.01)
  *C09K 11/06* (2006.01)
  *H10K 50/16* (2023.01)
  *H10K 50/17* (2023.01)
  *H10K 50/18* (2023.01)

(52) U.S. Cl.
  CPC ......... *C07D 251/24* (2013.01); *C07D 401/14* (2013.01); *C09K 11/06* (2013.01); *H10K 85/615* (2023.02); *H10K 85/626* (2023.02); *C09K 2211/1018* (2013.01); *H10K 50/16* (2023.02); *H10K 50/171* (2023.02); *H10K 50/18* (2023.02)

(56) References Cited

U.S. PATENT DOCUMENTS

| | | | |
|---|---|---|---|
| 2014/0299192 A1 | 10/2014 | Lee et al. | |
| 2015/0162543 A1* | 6/2015 | Lee | C07D 213/06 |
| | | | 136/263 |
| 2016/0141514 A1 | 5/2016 | Lee et al. | |
| 2018/0066180 A1 | 3/2018 | Huh et al. | |
| 2018/0134686 A1 | 5/2018 | Bergmann | |
| 2020/0181096 A1* | 6/2020 | Yang | C07D 401/14 |

FOREIGN PATENT DOCUMENTS

| | | | |
|---|---|---|---|
| KR | 10-2000-0051826 | 8/2000 | |
| KR | 10-2013-0135181 | 12/2013 | |
| KR | 10-2014-0009919 | 1/2014 | |
| KR | 10-2014-0094408 | 7/2014 | |
| KR | 10-2015-0002507 | 1/2015 | |
| KR | 10-2016-0025776 | 3/2016 | |
| KR | 10-2016-0111780 | 9/2016 | |
| KR | 10-2016-0126862 | 11/2016 | |
| KR | 10-2018-0048412 | 5/2018 | |
| WO | 2003-012890 | 2/2003 | |
| WO | WO-2019139233 A1 * | 7/2019 | ........... C07D 209/82 |
| WO | WO-2020071627 A1 * | 4/2020 | ........... C07D 213/57 |

* cited by examiner

[FIG. 1]
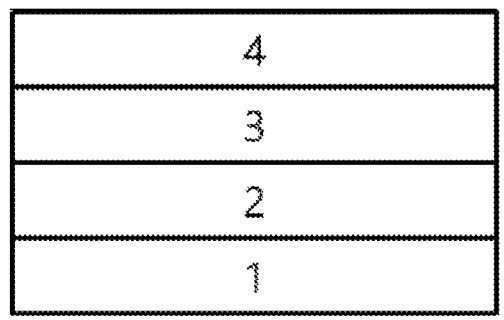
[FIG. 2]
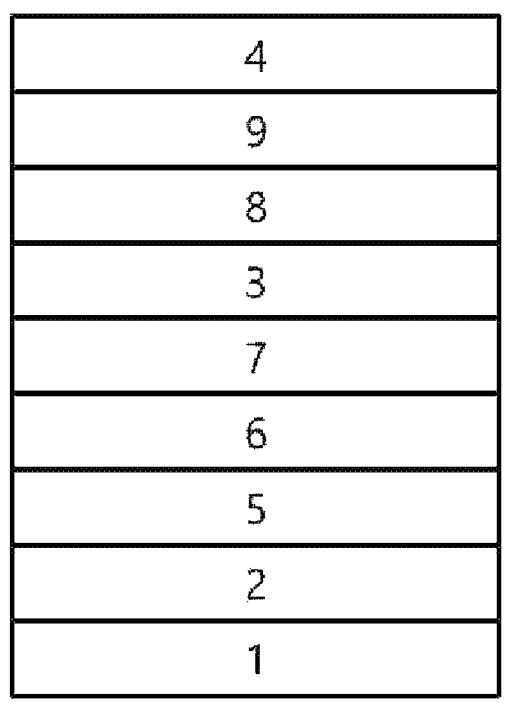

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/009675 filed on Aug. 2, 2019, which claims priority to and the benefit of the filing dates of Korean Patent Application No. 10-2018-0117683 filed with Korean Intellectual Property Office on Oct. 2, 2018, and Korean Patent Application No. 10-2019-0093314 filed with Korean Intellectual Property Office on Jul. 31, 2019, the entire contents of which are incorporated herein by reference.

TECHNICAL FIELD

The present invention relates to a novel compound and to an organic light emitting device including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer can be formed of a hole injection layer, a hole transport layer, a light emitting layer, a hole blocking layer, an electron transport layer, an electron injection layer, and the like. In the structure of the organic light emitting device, if a voltage is applied between two electrodes, holes are injected from an anode into the organic material layer and electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 1) Korean Patent Laid-open Publication No. 10-2000-0051826

BRIEF DESCRIPTION

Technical Problem

It is an object of the present invention to provide a novel compound and an organic light emitting device including the same.

Technical Solution

In one aspect of the invention, a compound of the following Chemical Formula 1 is provided:

Chemical Formula 1

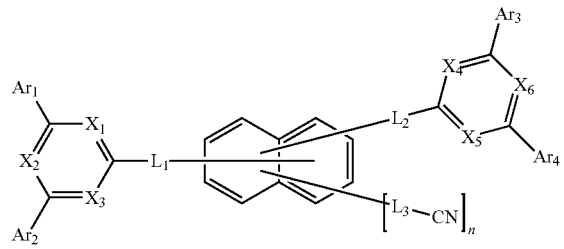

wherein, in Chemical Formula 1:
$X_1$ to $X_3$ are each independently N or CH, provided that at least one of $X_1$ to $X_3$ is N;
$X_4$ to $X_6$ are each independently N or CH, provided that at least one of $X_4$ to $X_6$ is N;
$Ar_1$ to $Ar_4$ are each independently a substituted or unsubstituted $C_{6-60}$ aryl, or a substituted or unsubstituted $C_{2-60}$ heteroaryl containing any one or more selected from the group consisting of N, O, and S;
$L_1$ to $L_3$ are each independently a single bond, a substituted or unsubstituted $C_{6-60}$ arylene, or a substituted or unsubstituted $C_{2-60}$ heteroarylene containing any one or more selected from the group consisting of N, O, and S; and
n is 1 or 2.

In another aspect of the invention, an organic light emitting device is provided, including: a first electrode; a second electrode provided to face the first electrode; and one or more organic material layers provided between the first electrode and the second electrode, wherein one or more layers of the organic material layers includes the compound of Chemical Formula 1.

Advantageous Effects

The compound of Chemical Formula 1 described above can be used as a material of an organic material layer of an organic light emitting device, and can improve the efficiency, achieve a low driving voltage, and/or improve lifetime characteristics in the organic light emitting device. In particular, the compound of Chemical Formula 1 described above can be used as a material for electron transport, electron injection, or hole blocking.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, an electron inhibition layer 7, a light emitting layer 3, a hole blocking layer 8, an electron injection and transport layer 9, and a cathode 4.

DETAILED DESCRIPTION

Hereinafter, the present invention will be described in more detail to help understanding of the present invention.

In one embodiment of the invention, the compound of Chemical Formula 1 is provided.

As used herein, the notation ⸺ means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group containing at least one of N, O, and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group, and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae, but is not limited thereto:

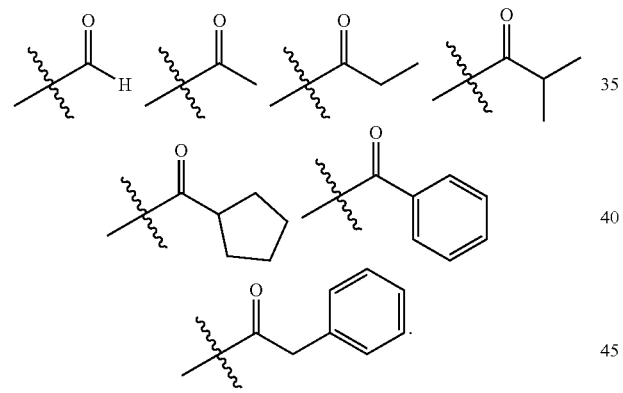

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

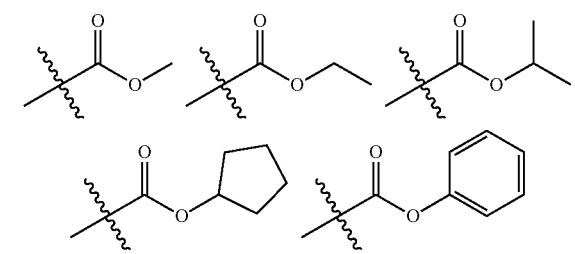

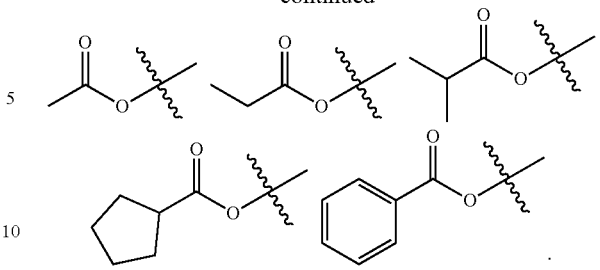

In the present specification, the number of carbon atoms of an imide group is not particularly limited, but is preferably 1 to 25. Specifically, the imide group can be a compound having the following structural formulae, but is not limited thereto:

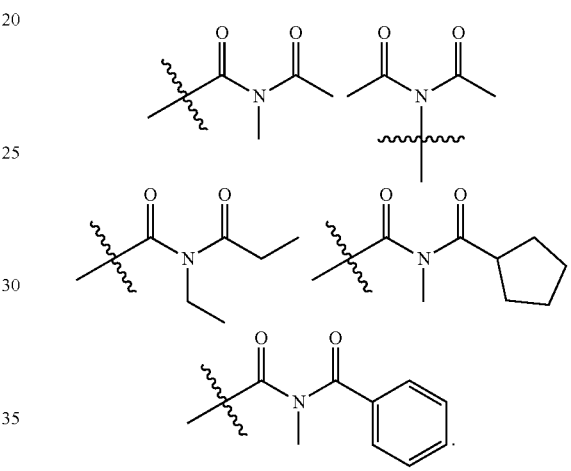

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexyl-methyl, octyl, n-octyl, tert-octyl, 1-methylheptyl, 2-ethylhexyl, 2-propylpentyl, n-nonyl, 2,2-dimethyl-heptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group can be substituted, and two substituent groups can be bonded to each other to form a spiro structure. In the case where the fluorenyl group is substituted,

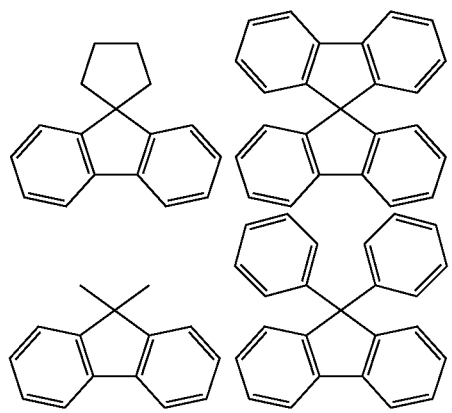

and the like can be formed. However, the structure is not limited thereto.

In the present specification, a heterocyclic group is one including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

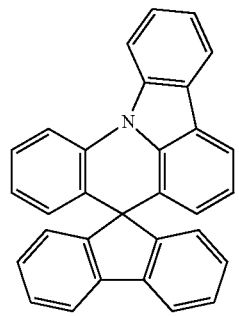

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

The compound can be any one of the following Chemical Formula 1-1 to Chemical Formula 1-5:

Chemical Formula 1-1

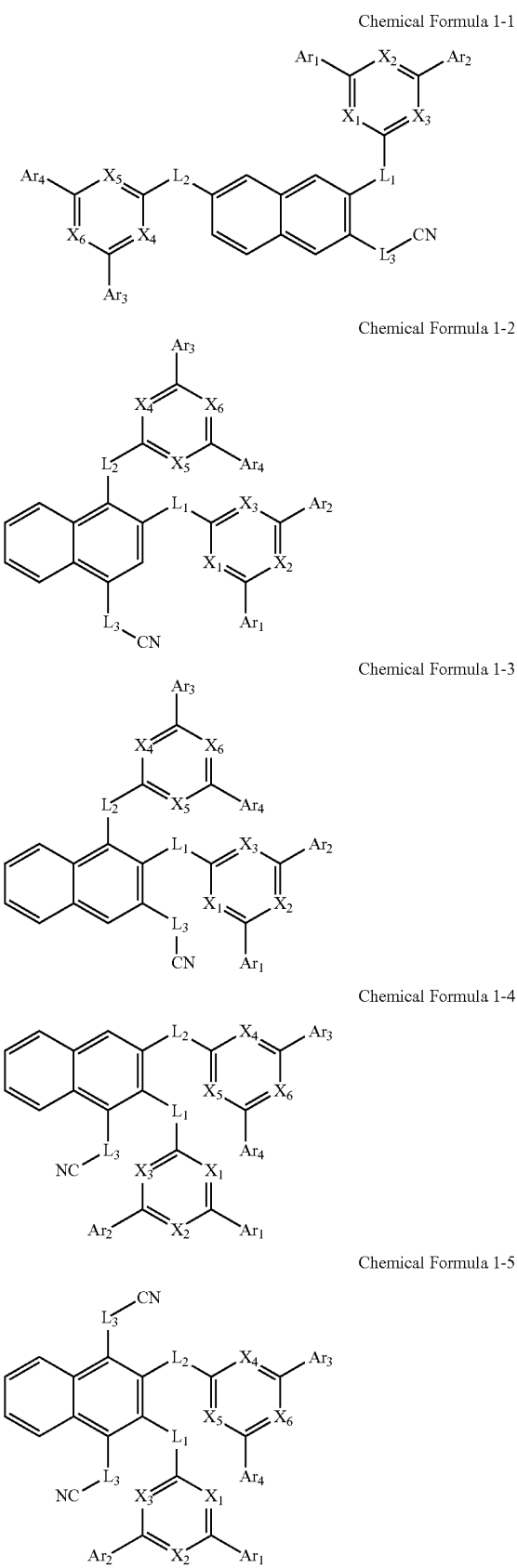

Chemical Formula 1-2

Chemical Formula 1-3

Chemical Formula 1-4

Chemical Formula 1-5 wherein, in Chemical Formulas 1-1 to 1-5, $X_1$ to $X_6$, $Ar_1$ to $Ar_4$ and $L_1$ to $L_3$ are the same as those defined in Chemical Formula 1.

Preferably, $Ar_1$ to $Ar_4$ can each independently be a substituted or unsubstituted $C_{6-20}$ aryl, or a substituted or unsubstituted $C_{6-20}$ heteroaryl containing any one or more selected from the group consisting of N, O, and S.

More preferably, $Ar_1$ to $Ar_4$ can each independently be phenyl, pyridinyl, biphenylyl, terphenylyl, naphthyl, or phenanthrenyl.

Preferably, $Ar_1$ and $Ar_3$ can be the same as each other, and $Ar_2$ and $Ar_4$ can be the same as each other.

Preferably, $L_1$ and $L_2$ can be the same as each other.

Preferably, $L_1$ to $L_3$ can each independently be a single bond; a substituted or unsubstituted $C_{6-20}$ arylene; or a substituted or unsubstituted $C_{6-20}$ heteroarylene containing any one or more selected from the group consisting of N, O, and S.

More preferably, $L_1$ to $L_3$ can each independently be a single bond, phenylene, biphenylylene, terphenylene, or naphthylene.

Preferably, at least one of $L_1$ to $L_3$ can be phenylene.

Representative examples of the compound of Chemical Formula 1 are as follows:

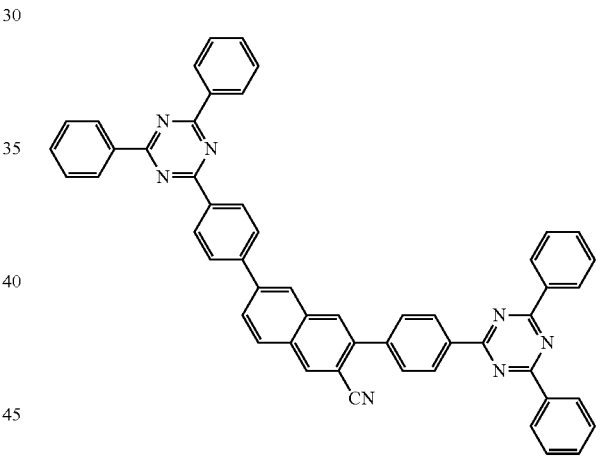

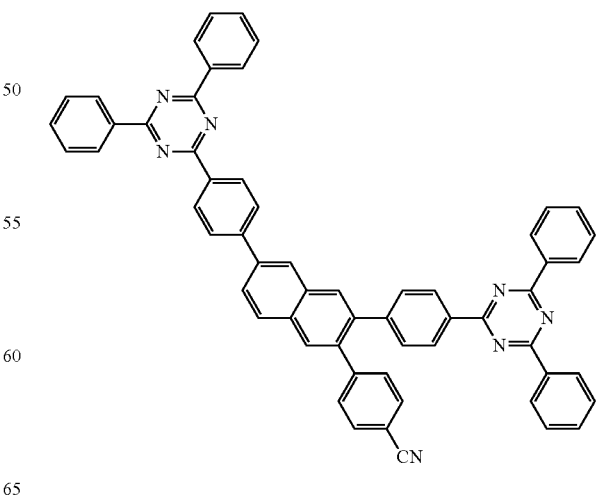

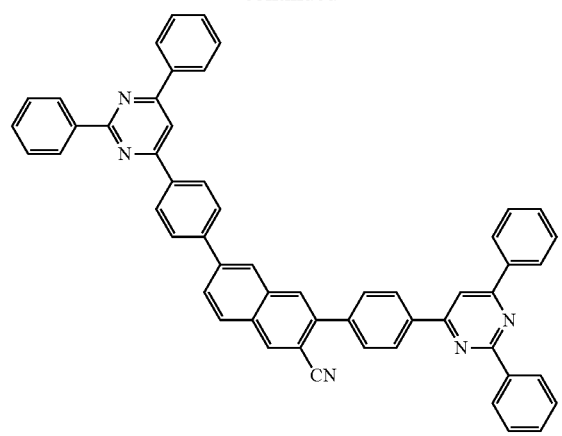
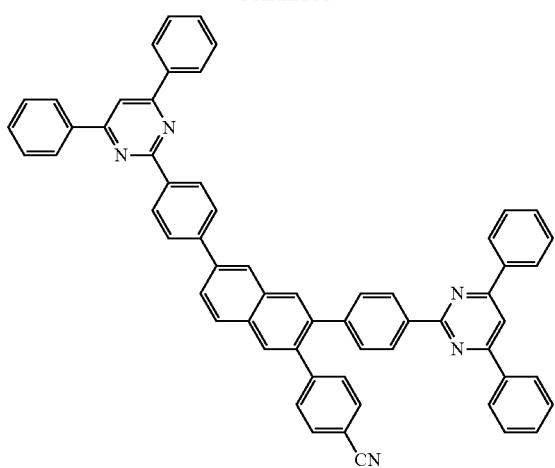
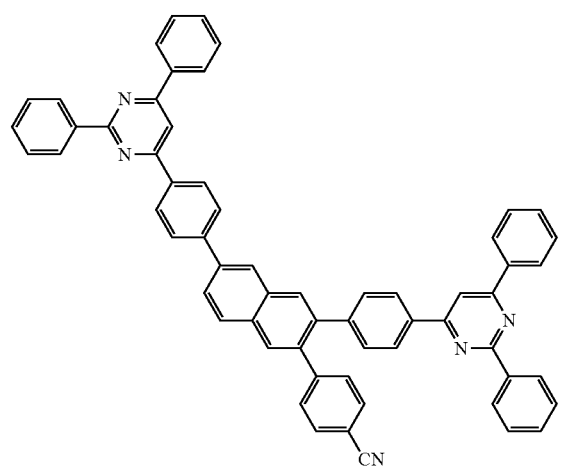
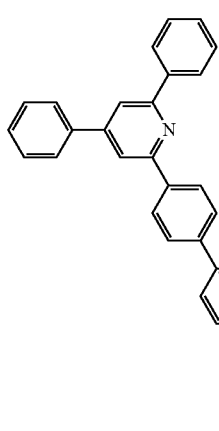
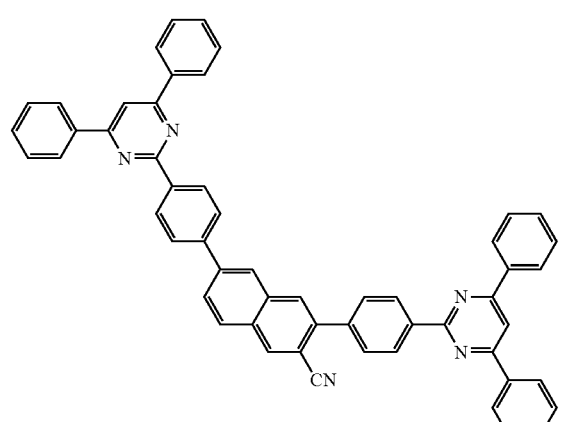
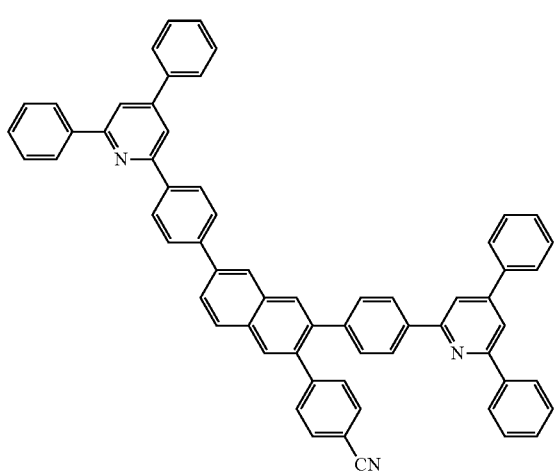

-continued
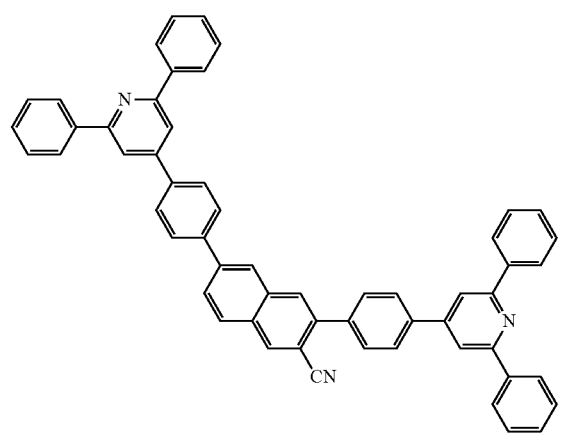
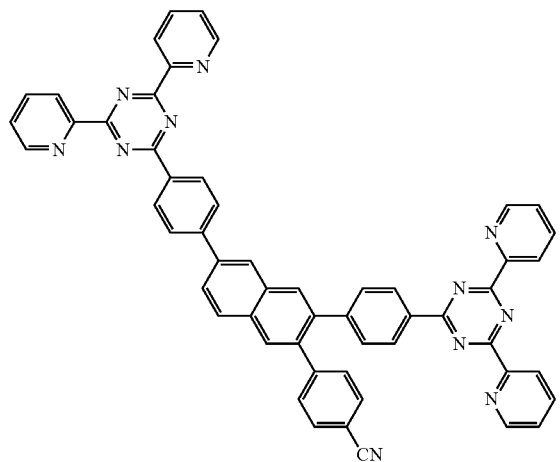
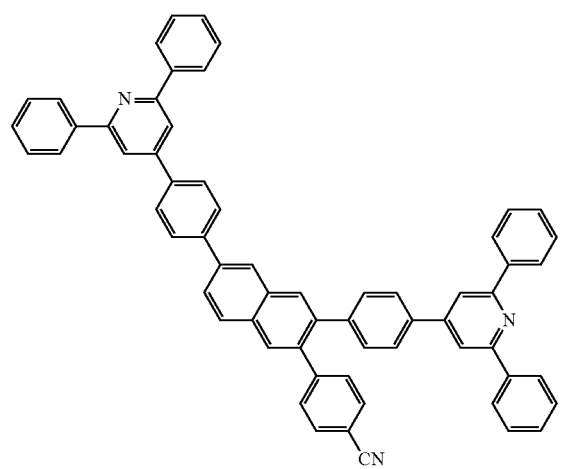
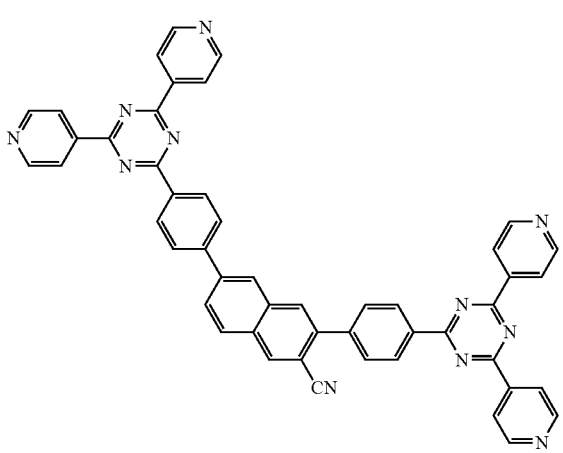
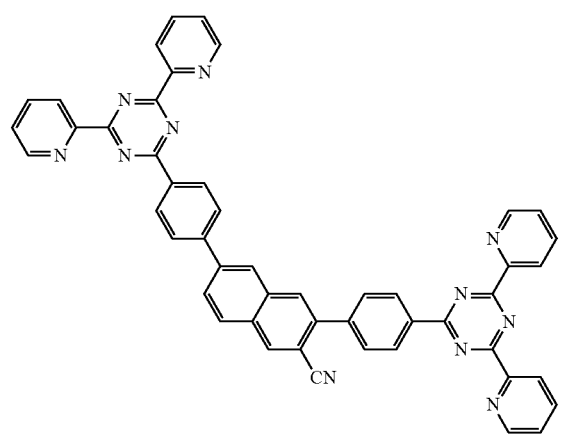
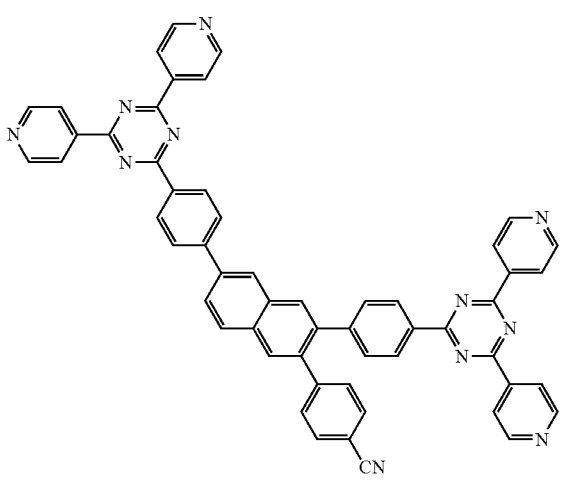

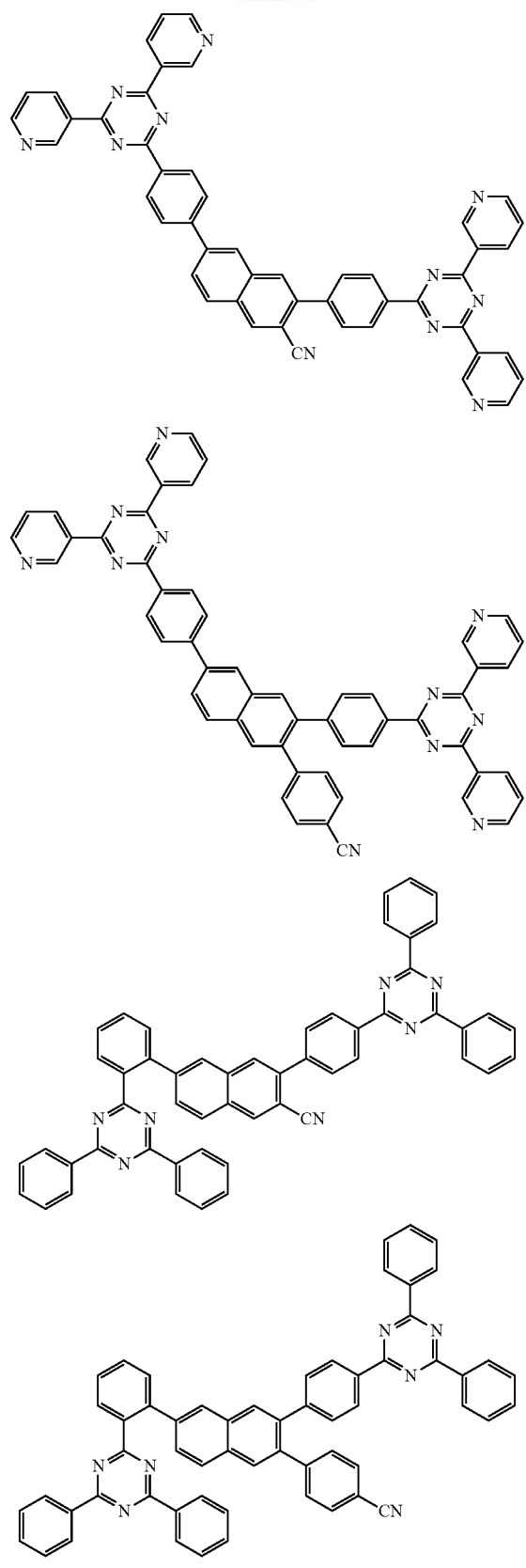
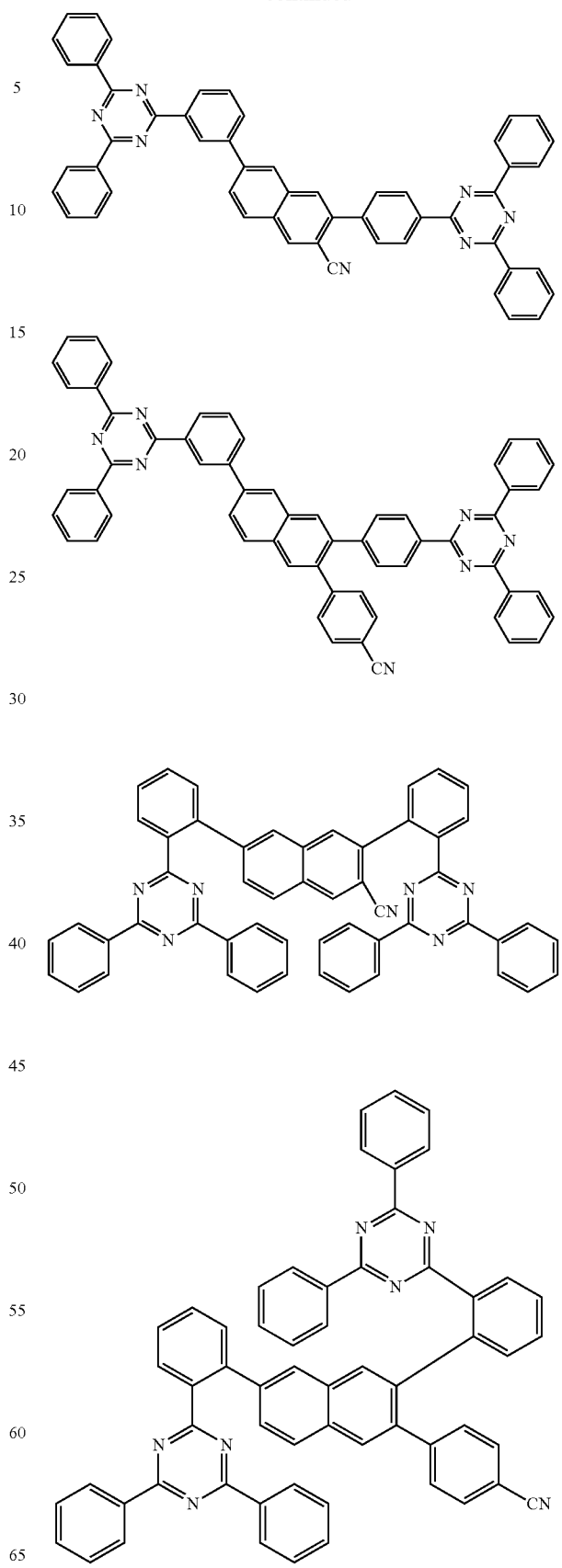

-continued
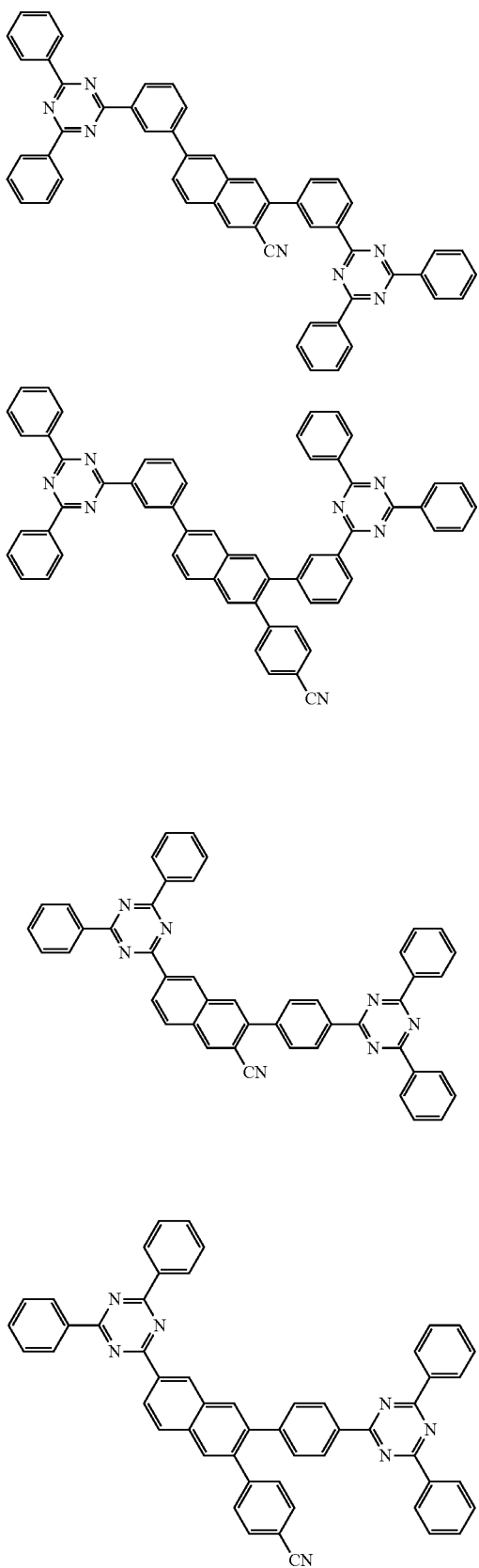
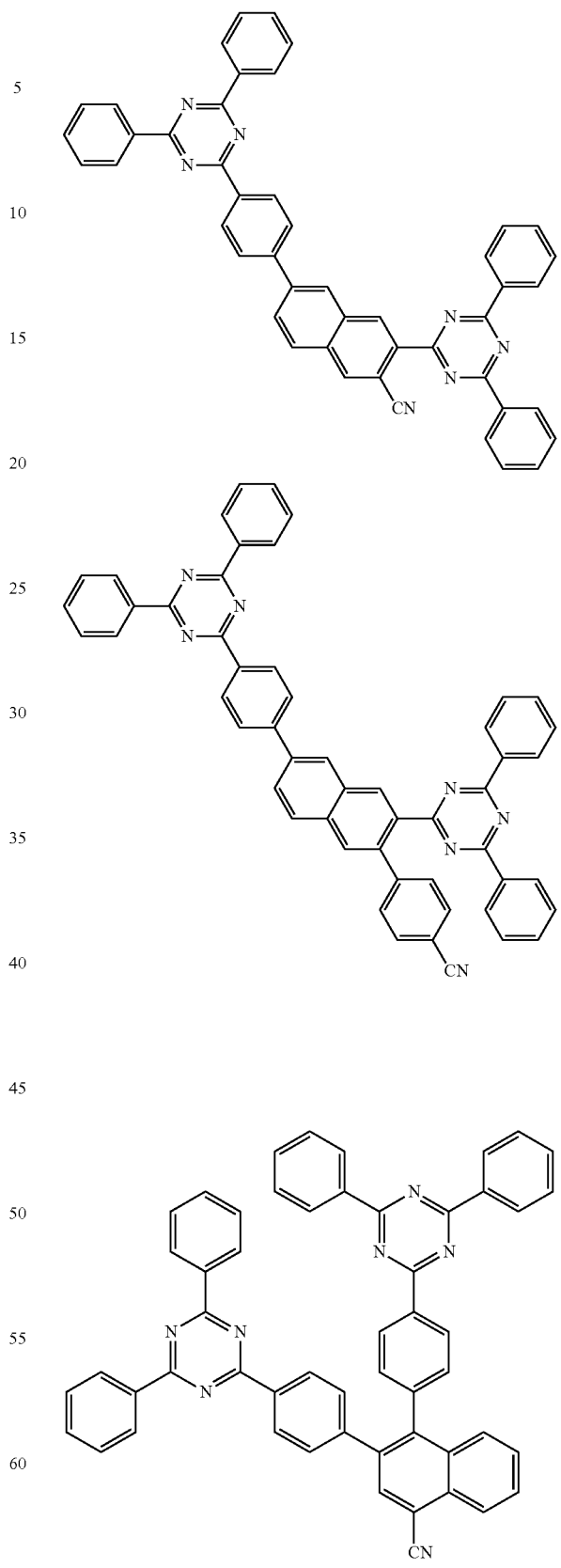

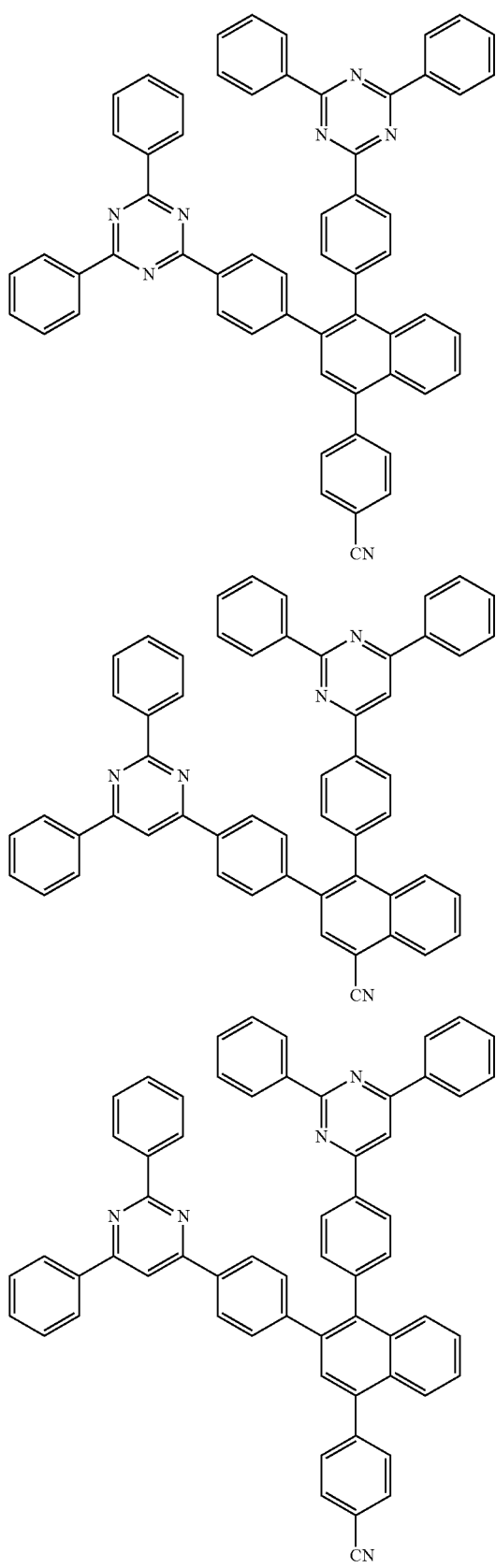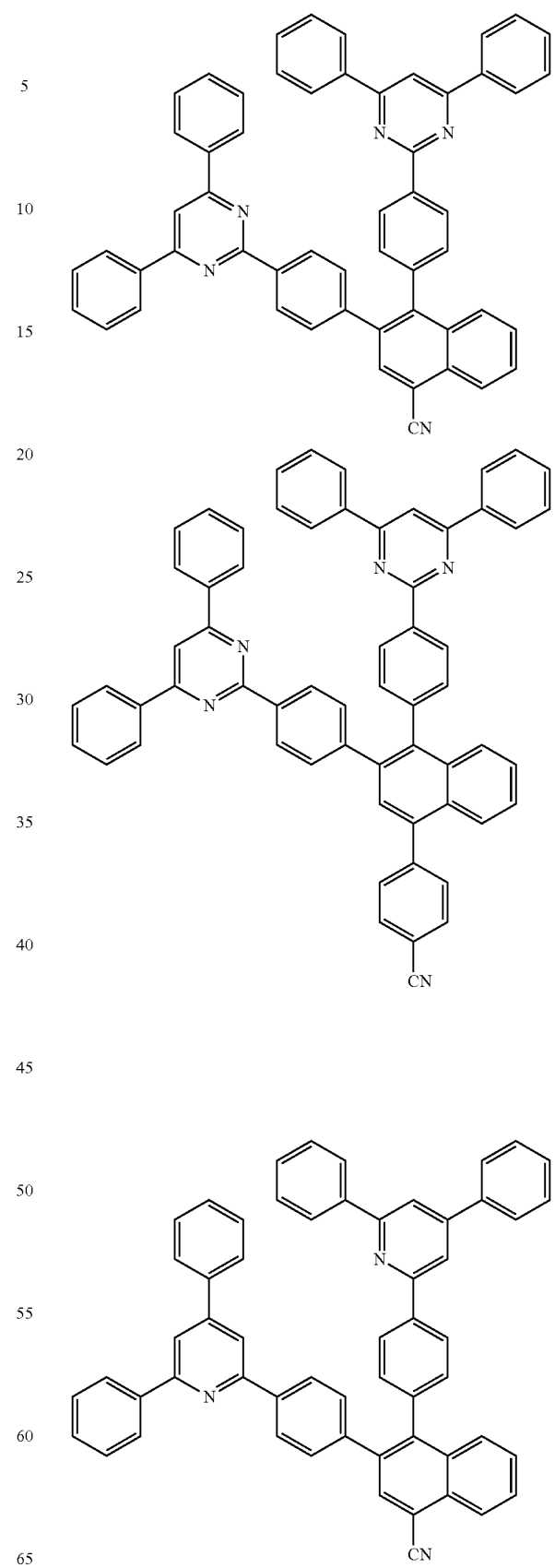

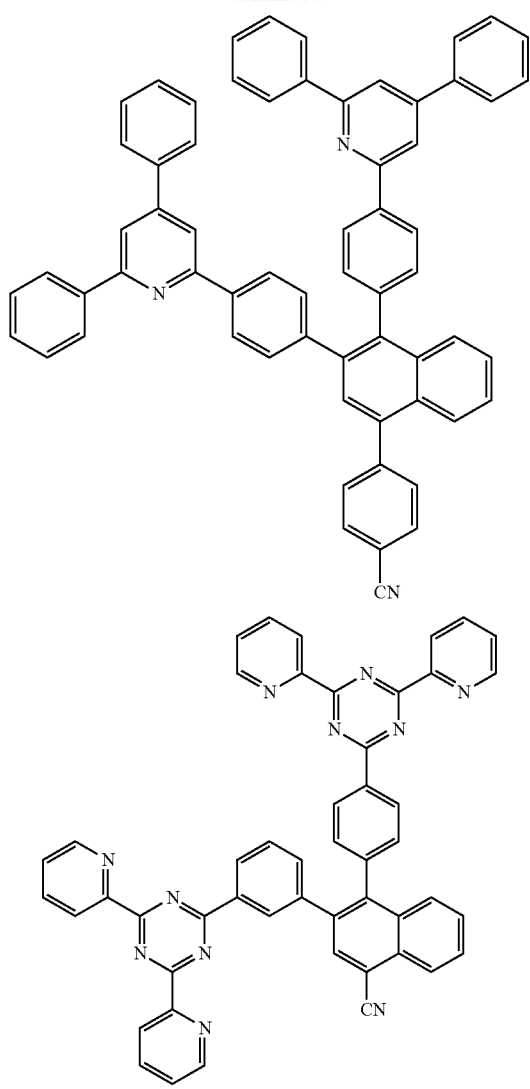
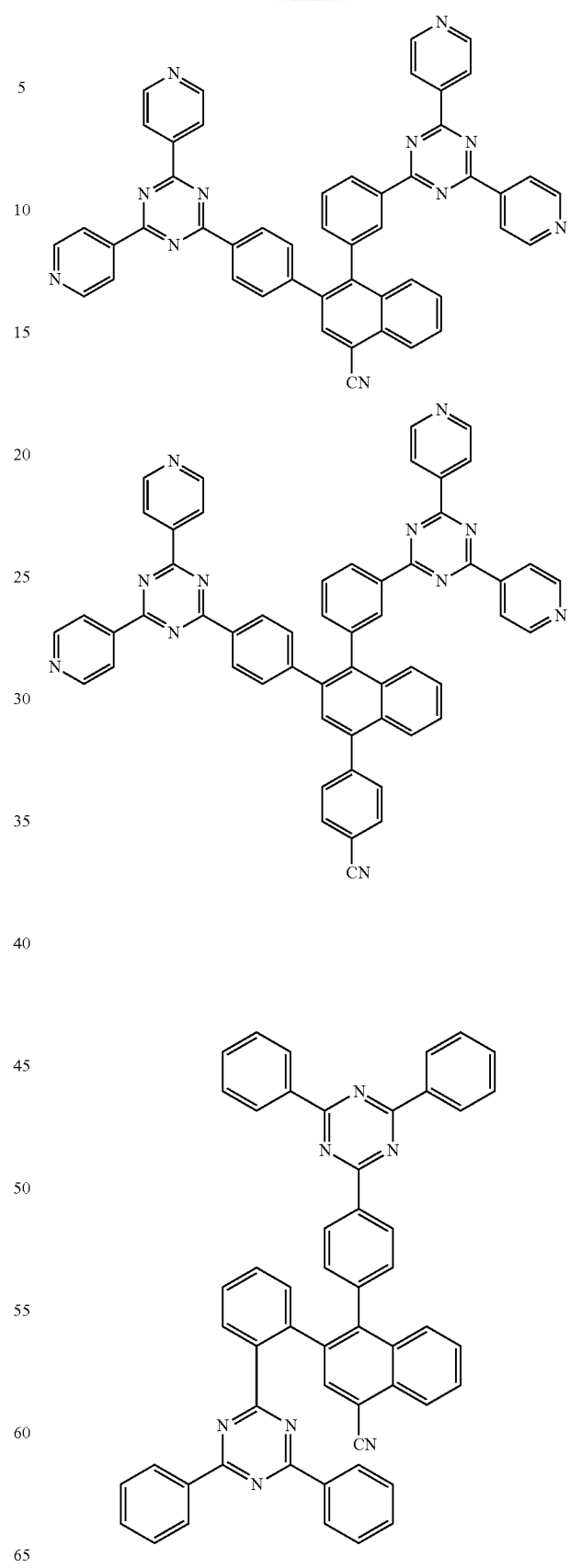

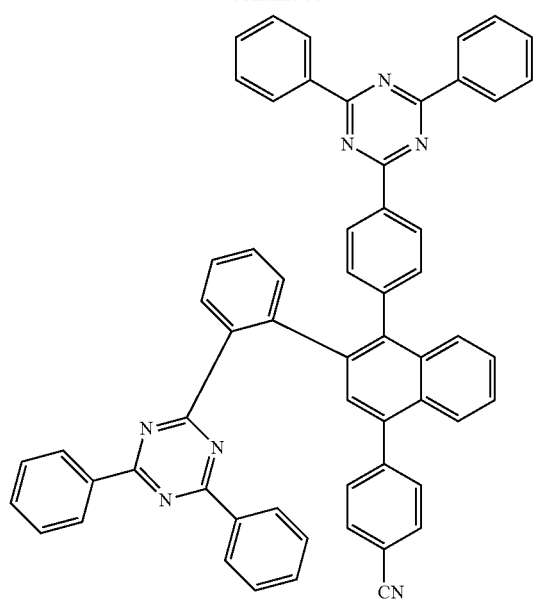
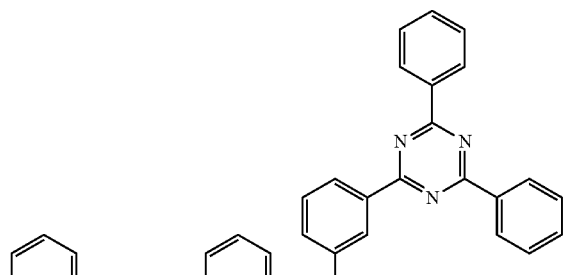
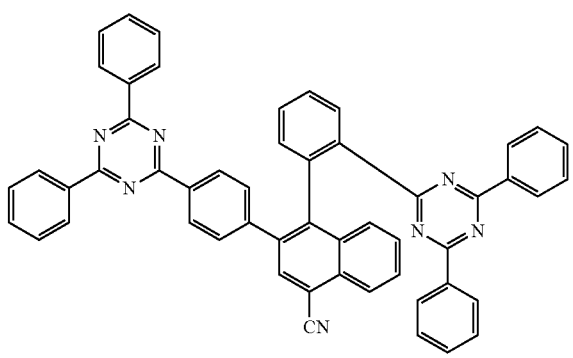
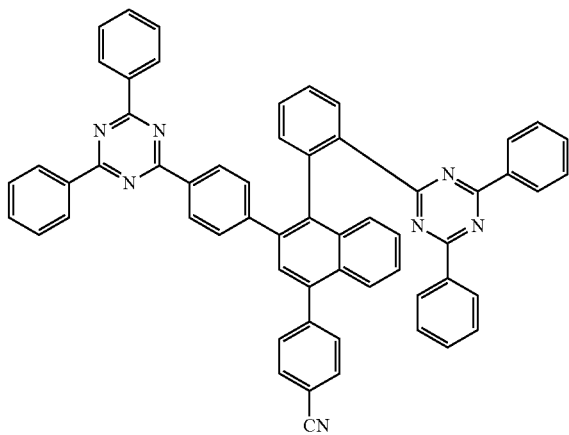
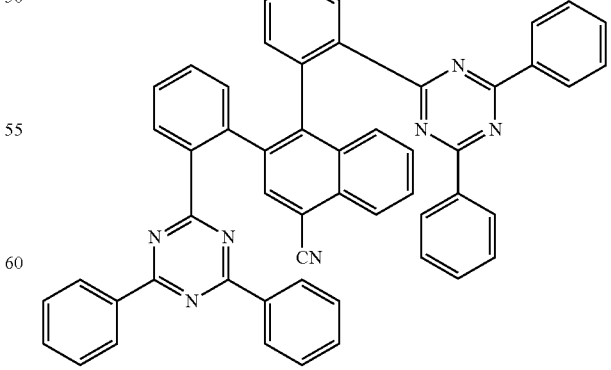

23
-continued
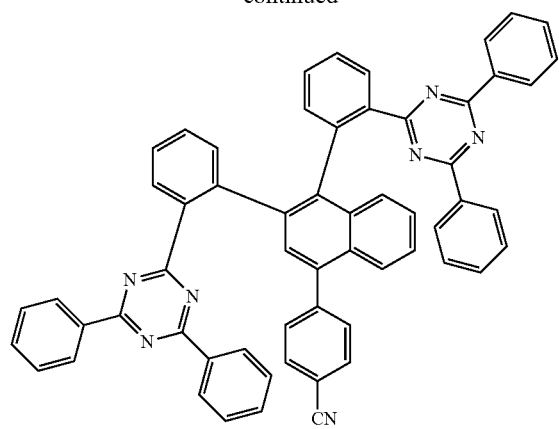
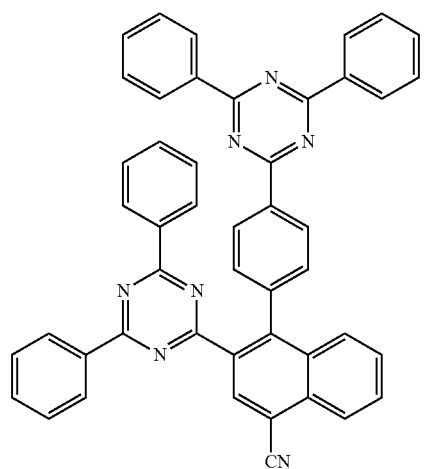
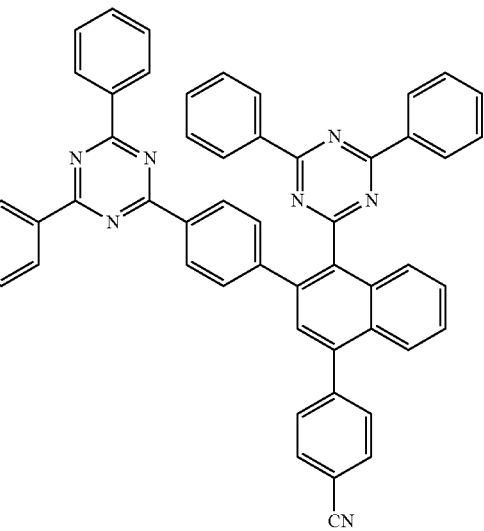
24
-continued
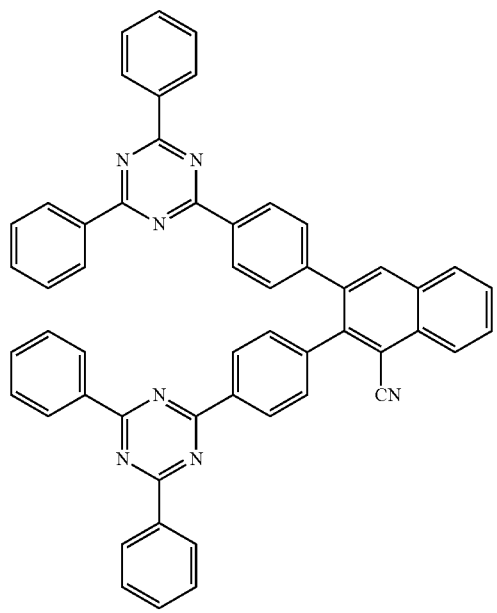
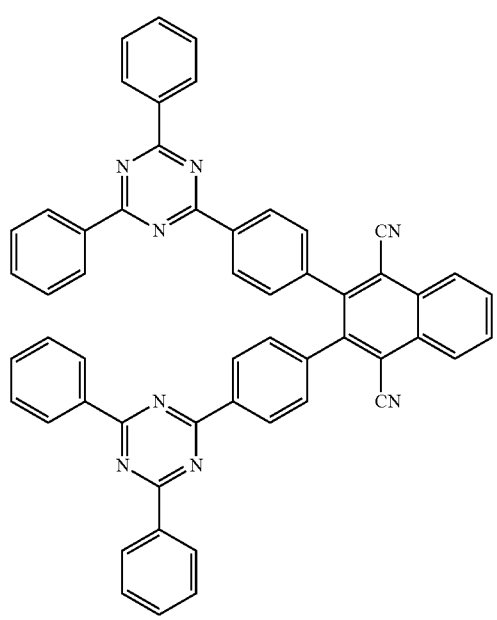

-continued
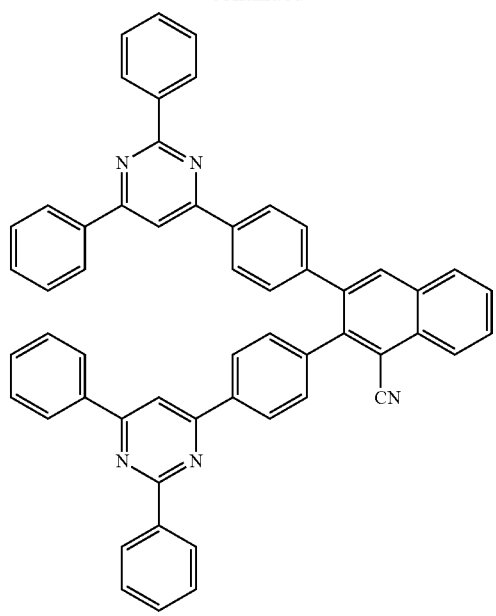
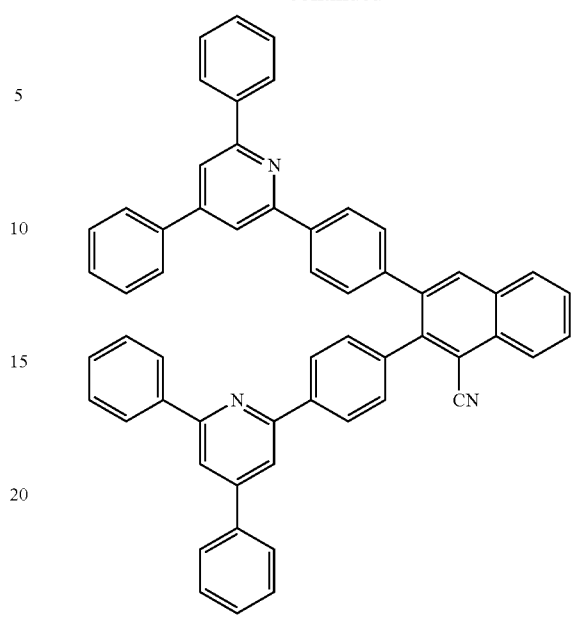

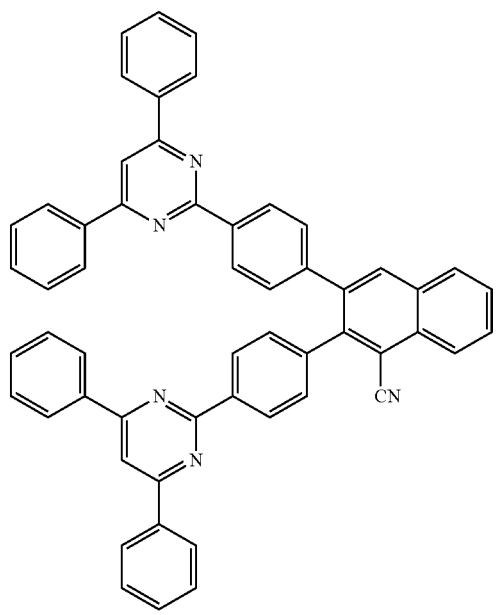
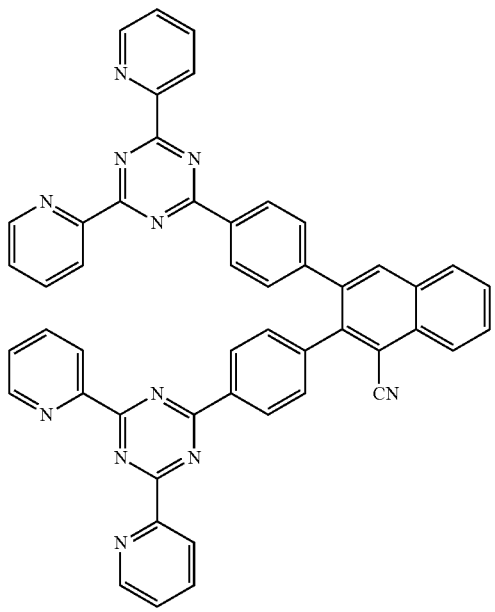
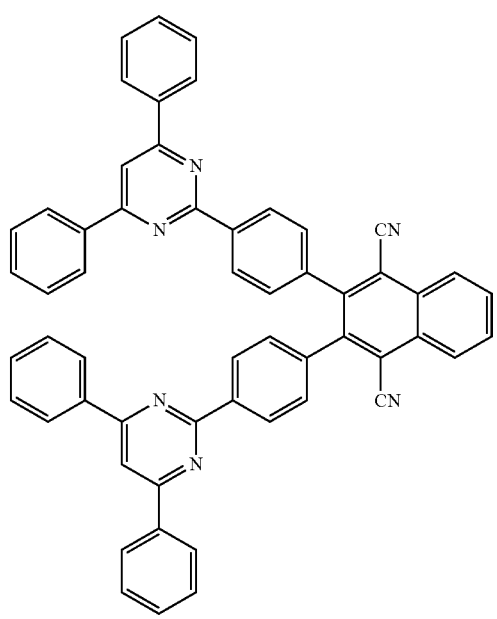
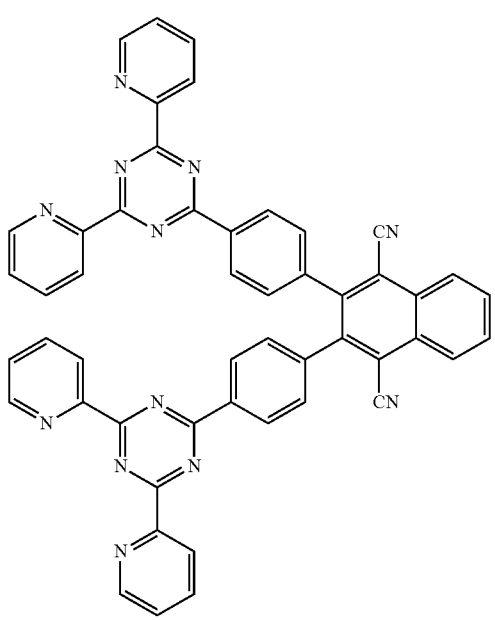

29
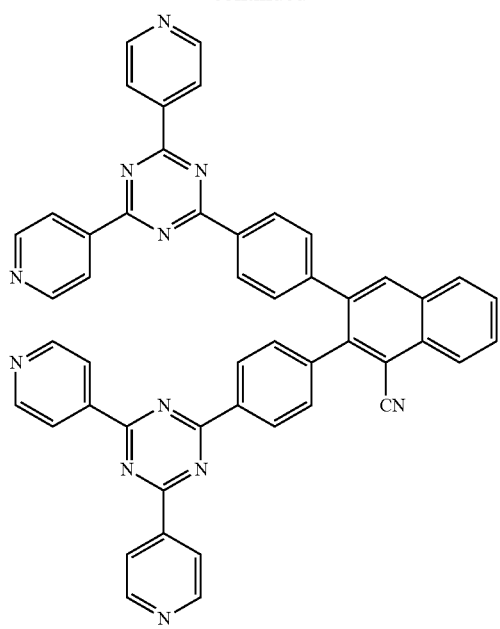
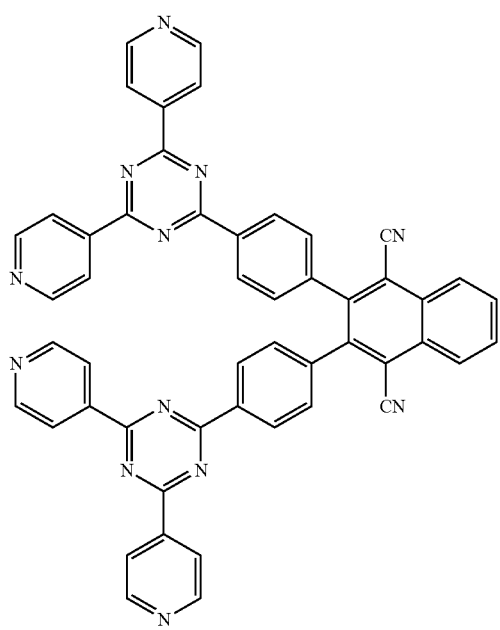
30
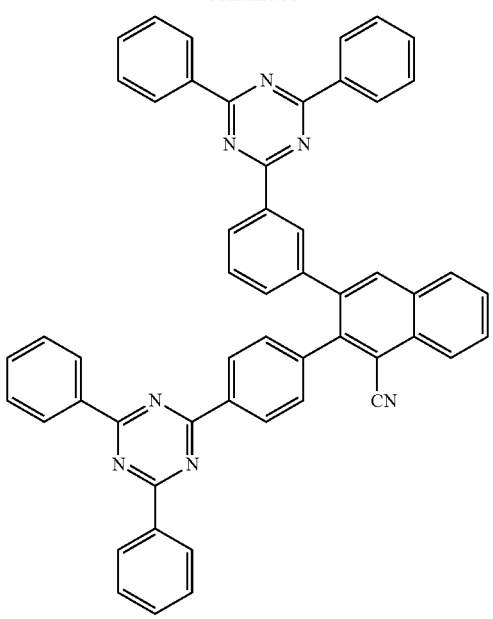
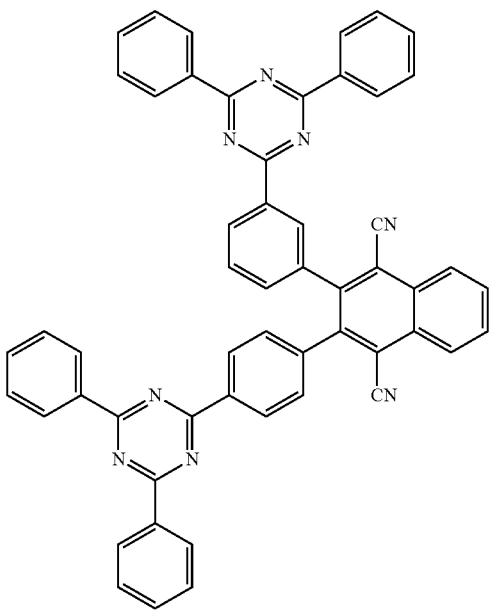

31
-continued
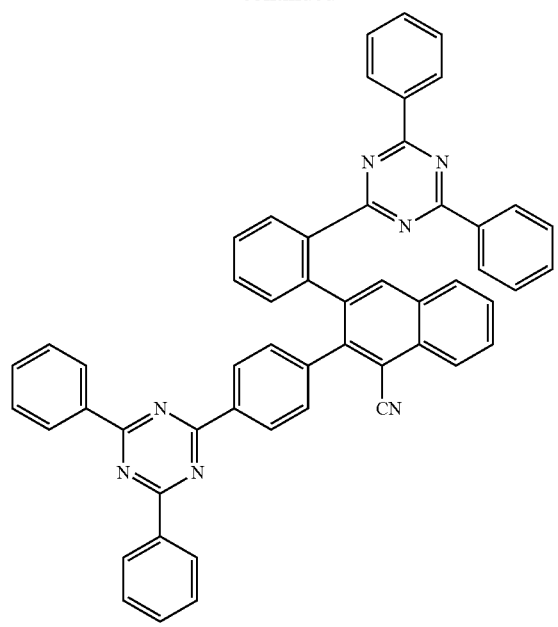
32
-continued
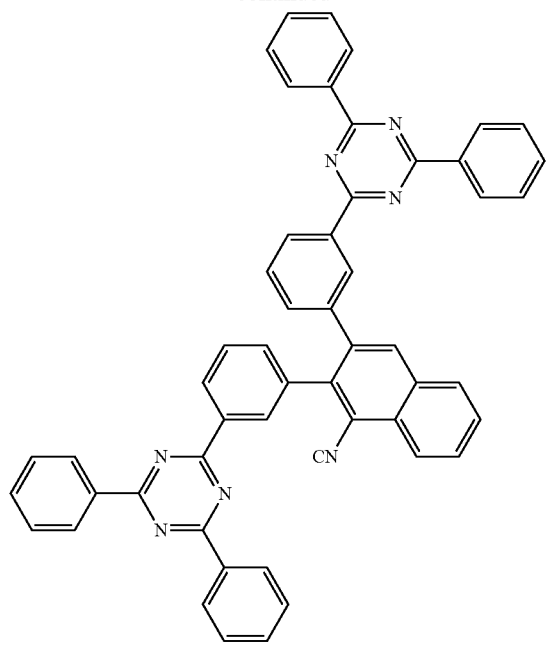
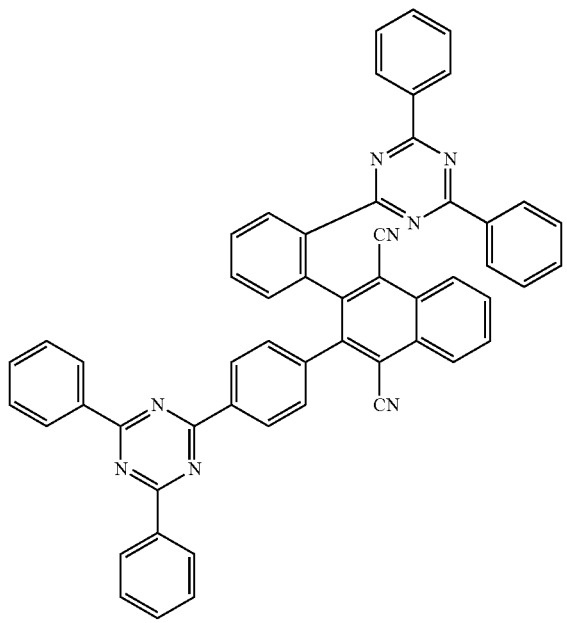
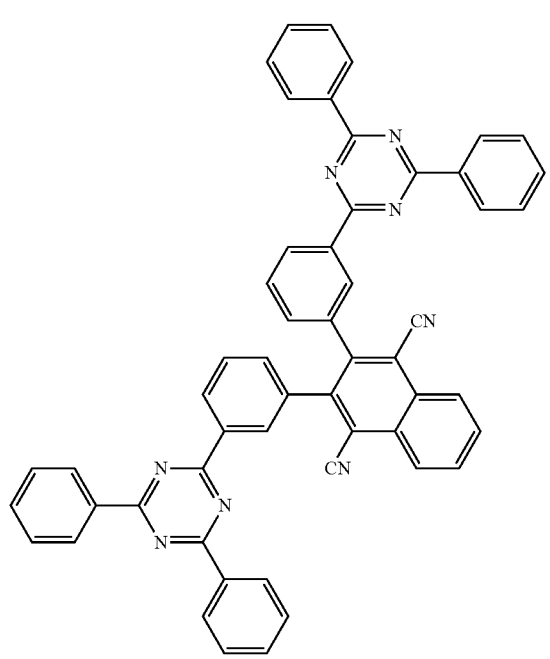

33
-continued
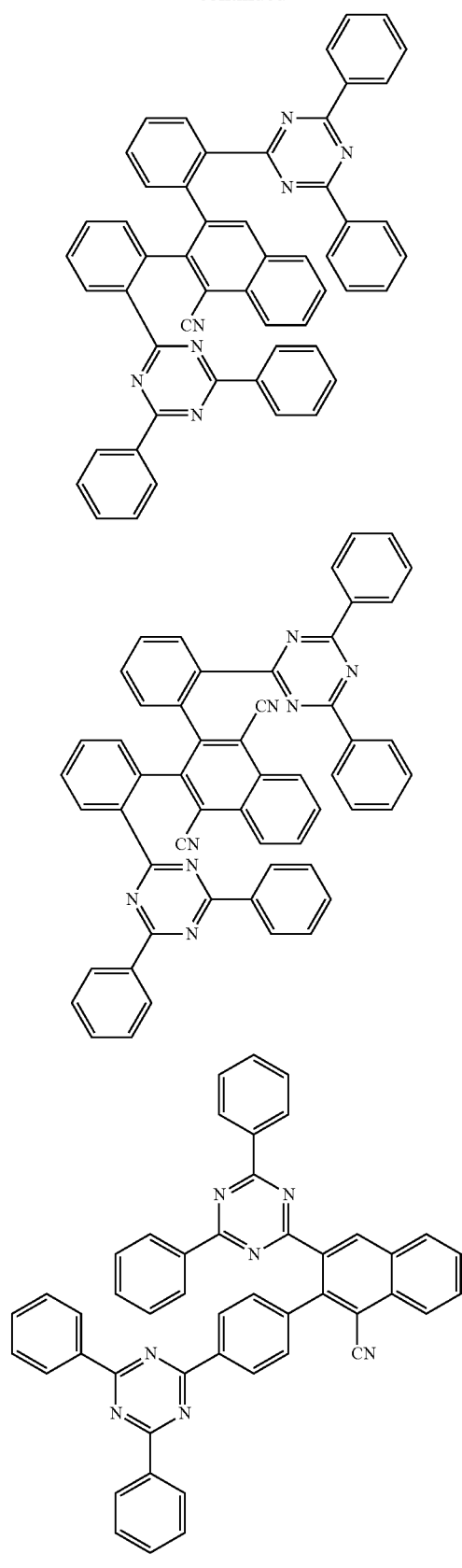
34
-continued
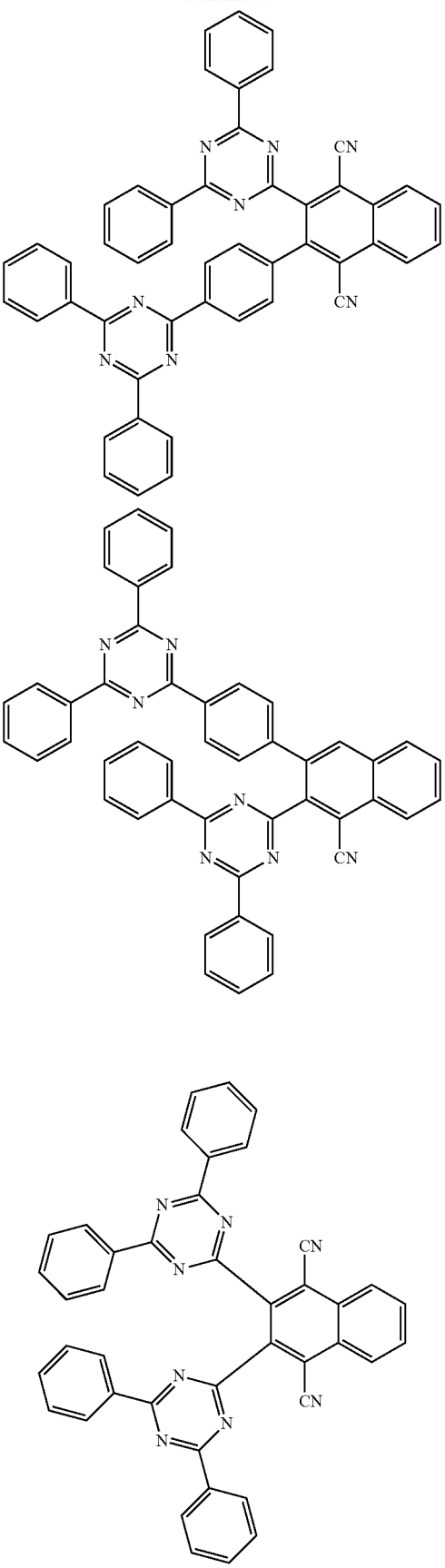

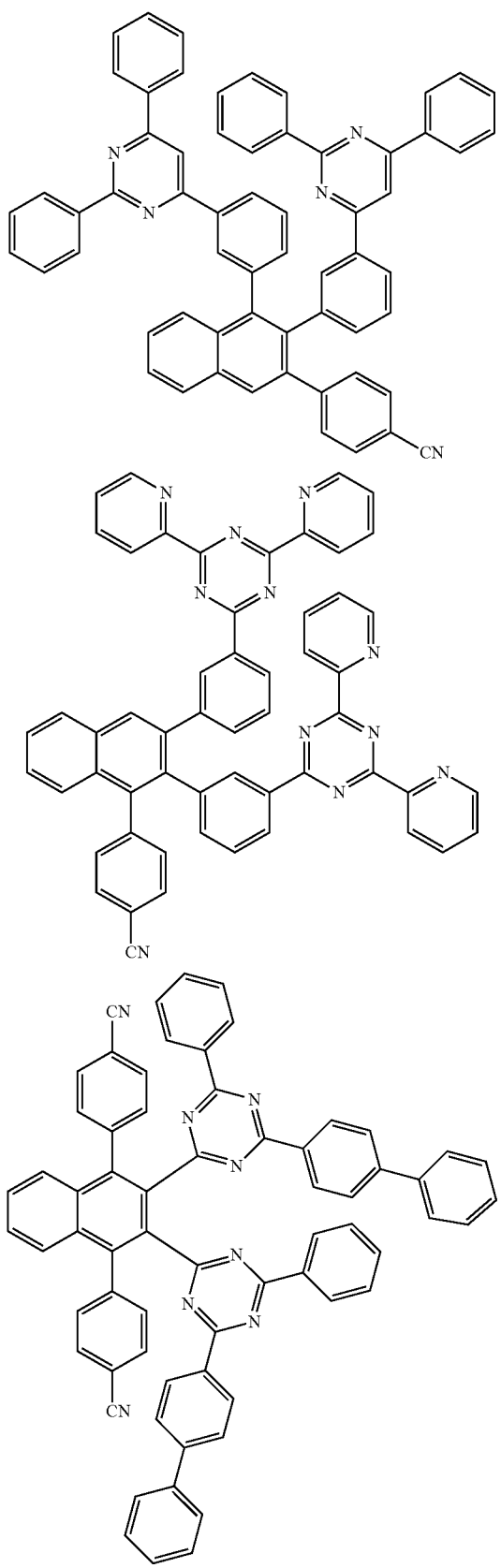
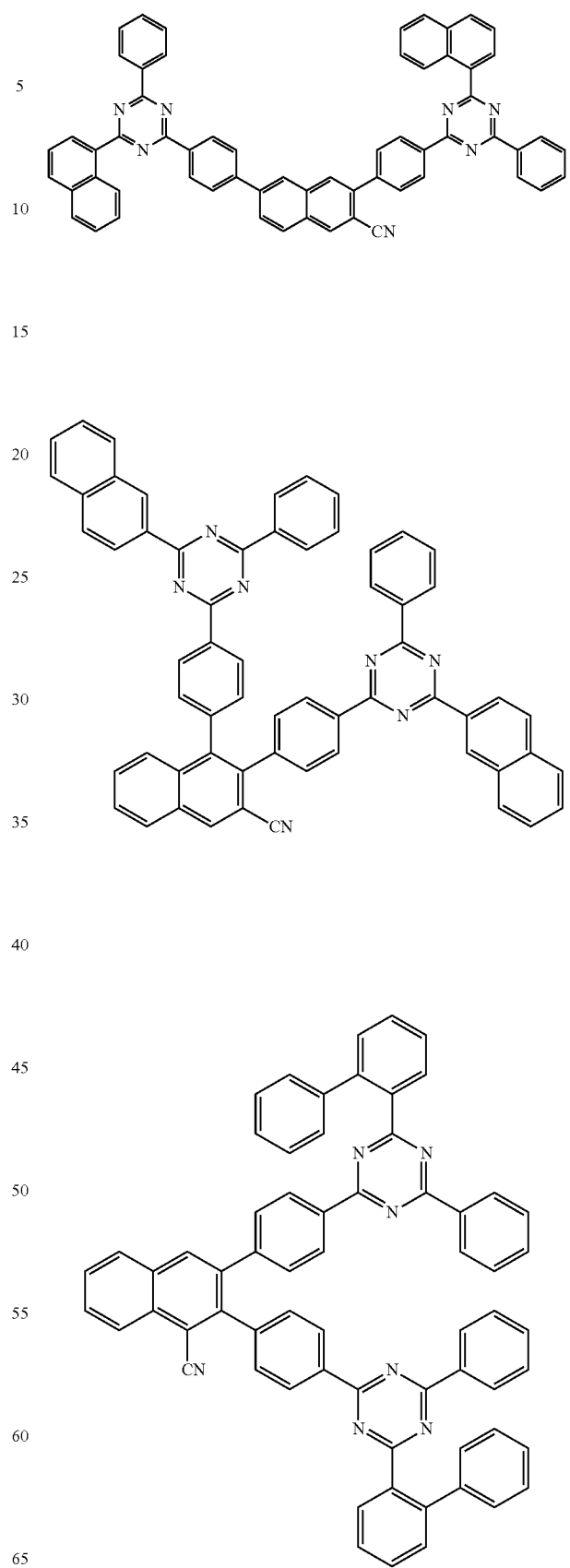

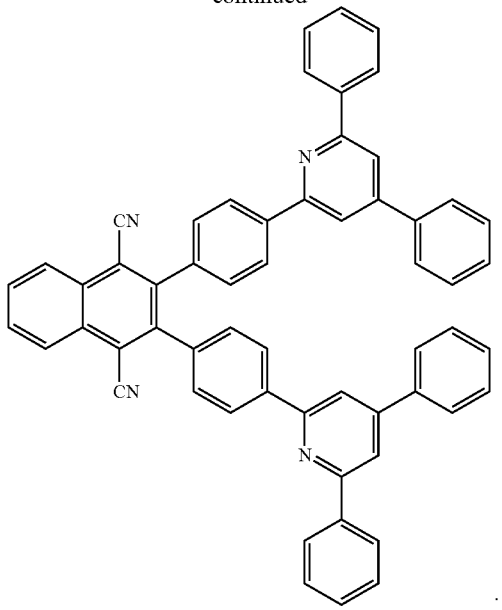 [SMILES: N#Cc1c(-c2ccc(-c3cc(-c4ccccc4)cc(-c4ccccc4)n3)cc2)c(-c2ccc(-c3cc(-c4ccccc4)cc(-c4ccccc4)n3)cc2)c(C#N)c2ccccc12]

When the compound of Chemical Formula 1 is Chemical Formula 1-1, the compound can be prepared, for example, according to the preparation method as shown in the following Reaction Scheme 1, and the remaining compounds can be prepared in a similar manner.

Reaction Scheme 1

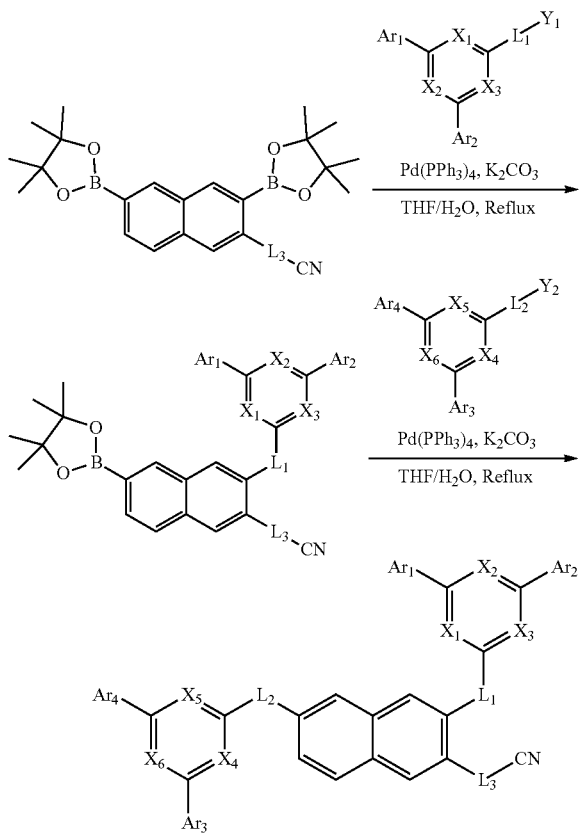

In Reaction Scheme 1 above, $X_1$ to $X_6$, $Ar_1$ to $Ar_4$, and $L_1$ to $L_3$ are as defined above, $Y_1$ and $Y_2$ are each a halogen, and preferably, $Y_1$ and $Y_2$ are chloro or bromo.

Reaction Scheme 1 is a Suzuki coupling reaction, which is preferably carried out in the presence of a palladium catalyst and a base, and a reactive group for the Suzuki coupling reaction can be modified as known in the art. The above preparation method can be further specified in preparation examples described hereinafter.

In another embodiment of the invention, an organic light emitting device including the compound of Chemical Formula 1 described above is provided. As an example, an organic light emitting device is provided, including: a first electrode; a second electrode provided to face the first electrode; and one or more organic material layers provided between the first electrode and the second electrode, wherein one or more layers of the organic material layers include the compound of Chemical Formula 1.

The organic material layer of the organic light emitting device of the present invention can have a single layer structure, or it can have a multilayered structure in which two or more organic material layers are stacked. For example, the organic light emitting device of the present invention can have a structure including a hole transport layer, a light emitting layer, a hole blocking layer, an electron transport layer, an electron injection layer, and the like as the organic material layer. However, the structure of the organic light emitting device is not limited thereto, and it can include a smaller number of organic layers.

Further, the organic material layer can include a hole injection layer, a hole transport layer, or a layer for simultaneously performing hole injection and transport, wherein the hole injection layer, the hole transport layer, or the layer for simultaneously performing hole injection and transport can include the compound of Chemical Formula 1.

The organic material layer can include a light emitting layer, wherein the light emitting layer can include the compound of Chemical Formula 1.

The organic material layer can include a hole blocking layer, wherein the hole blocking layer can include the compound of Chemical Formula 1.

The organic material layer can include an electron transport layer, an electron injection layer, or a layer for simultaneously performing electron transport and electron injection, wherein the electron transport layer, the electron injection layer, or the layer for simultaneously performing electron transport and electron injection can include the compound of Chemical Formula 1.

The organic material layer can include a hole injection layer, a hole transport layer, an electron inhibition layer, a light emitting layer, a hole blocking layer, and an electron injection and transport layer, wherein any one or more selected from the group consisting of the hole injection layer, the hole transport layer, the electron inhibition layer, the light emitting layer, the hole blocking layer, and the electron injection and transport layer can include the compound of Chemical Formula 1.

The organic light emitting device according to the present invention can be a normal type of organic light emitting device in which an anode, one or more organic material layers, and a cathode are sequentially stacked on a substrate. Further, the organic light emitting device according to the present invention can be an inverted type of organic light emitting device in which a cathode, one or more organic material layers, and an anode are sequentially stacked on a substrate. For example, the structure of an organic light emitting device according to an embodiment of the present invention is illustrated in FIGS. 1 and 2.

FIG. 1 shows an example of an organic light emitting device including a substrate 1, an anode 2, a light emitting layer 3, and a cathode 4. In such a structure, the compound of Chemical Formula 1 can be included in the light emitting layer.

FIG. 2 shows an example of an organic light emitting device including a substrate 1, an anode 2, a hole injection layer 5, a hole transport layer 6, an electron inhibition layer 7, a light emitting layer 3, a hole blocking layer 8, an electron injection and transport layer 9, and a cathode 4. In such a structure, the compound of Chemical Formula 1 can be included in one or more layers of the hole injection layer, the hole transport layer, the electron inhibition layer, the light emitting layer, the hole blocking layer, and the electron injection and transport layer.

The organic light emitting device according to the present invention can be manufactured by materials and methods known in the art, except that one or more layers of the organic material layers include the compound of Chemical Formula 1. In addition, when the organic light emitting device includes a plurality of organic material layers, the organic material layers can be formed of the same material or different materials.

For example, the organic light emitting device according to the present invention can be manufactured by sequentially stacking a first electrode, an organic material layer, and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer, and an anode material on a substrate.

In addition, the compound of Chemical Formula 1 can be formed into an organic layer by a solution coating method as well as a vacuum deposition method at the time of manufacturing an organic light emitting device. Herein, the solution coating method means a spin coating method, a dip coating method, a doctor blading method, an inkjet printing method, a screen printing method, a spray method, a roll coating method, or the like, but is not limited thereto.

In addition to such a method, the organic light emitting device can be manufactured by sequentially depositing a cathode material, an organic material layer and an anode material on a substrate (International Publication WO2003/012890) However, the manufacturing method is not limited thereto.

As an example, the first electrode is an anode and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as ZnO:Al or SnO$_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron inhibition layer is a layer provided between the hole transport layer and the light emitting layer in order to prevent the electrons injected from the cathode from being transferred to the hole transport layer without being recombined in the light emitting layer, which can also be referred to as an electron blocking layer. The electron inhibition layer is preferably a material having a smaller electron affinity than the electron transport layer.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex (Alq$_3$); a carbazole-based compound; a dimerized styryl compound; BAlq; a 10-hydroxybenzoquinoline-metal compound; a benzoxazole, benzothiazole, and benzimidazole-based compound; a poly(p-phenylene vinylene) (PPV)-based polymer; a spiro compound; polyfluorene; rubrene; and the like, but are not limited thereto.

The light emitting layer can include a host material and a dopant material. The host material can be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryl diamine, styryl triamine, styryl tetramine, and the like, but are not limited thereto. Further, the metal complex includes an iridium complex, a platinum complex, and the like, but is not limited thereto.

The hole blocking layer is a layer provided between the electron transport layer and the light emitting layer in order to prevent the holes injected from the anode from being transferred to the electron transport layer without being recombined in the light emitting layer, which can also be referred to as a hole inhibition layer. The hole blocking layer is preferably a material having large ionization energy. Preferably, the compound of Chemical Formula 1 can be included as a material of the hole blocking layer.

The electron transport layer is a layer which receives electrons from an electron injection layer and transports the electrons to a light emitting layer, and an electron transport material is suitably a material which can receive electrons well from a cathode and transfer the electrons to a light emitting layer, and has large mobility for electrons. Specific examples thereof include: an Al complex of 8-hydroxyquinoline; a complex including $Alq_3$; an organic radical compound; a hydroxyflavone-metal complex; and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxy-quinolinato)zinc, bis(8-hydroxyquinolinato)copper, bis(8-hydroxyquinolinato)manganese, tris(8-hydroxy-quinolinato)aluminum, tris(2-methyl-8-hydroxy-quinolinato)aluminum, tris(8-hydroxyquinolinato)-gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium, and the like, but are not limited thereto.

The organic light emitting device according to the present invention can be a front emission type, a rear emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only, and are not intended to limit the scope of the present invention.

Preparation Example 1: Preparation of Compound 1

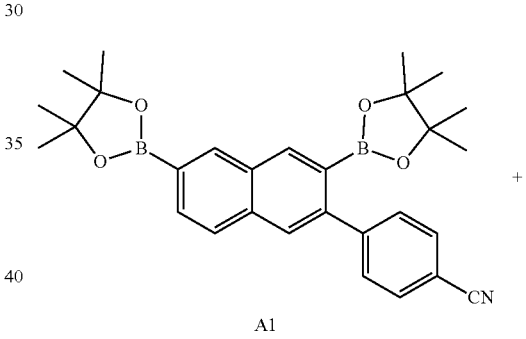

A1

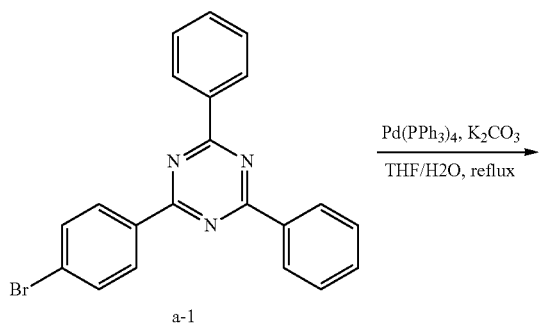

a-1

-continued

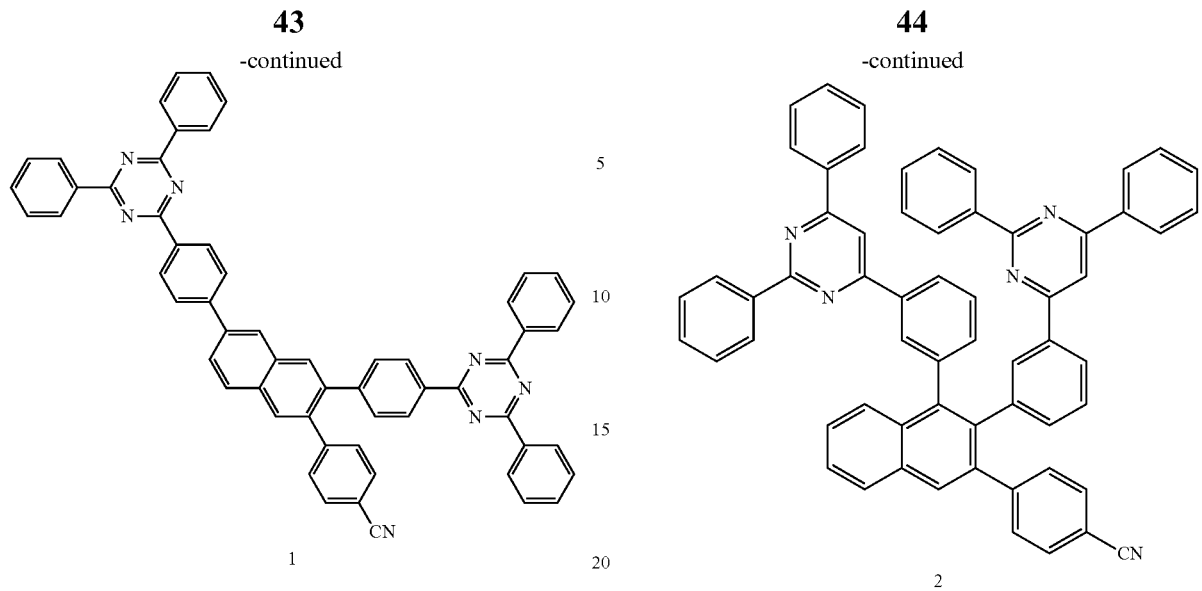

1

Compound A-1 (5.05 g, 10.49 mmol) and Compound a-1 (8.12 g, 20.98 mmol) were completely dissolved in 240 mL of tetrahydrofuran in a 500-ml round bottom flask under a nitrogen atmosphere, to which a 2M aqueous potassium carbonate solution (120 ml) was added and tetrakis-(triphenylphosphine)palladium (0.73 g, 0.63 mmol) was added, and then the resulting mixture was heated and stirred for 9 hours. The temperature was lowered to normal temperature, the aqueous layer was removed, and the resulting product was dried over anhydrous magnesium sulfate, then concentrated under reduced pressure, and recrystallized with 360 mL of ethylacetate to prepare Compound 1 (12.22 g, yield: 69%).

MS: $[M+H]^+=845$

Preparation Example 2: Preparation of Compound 2

-continued

2

Compound A-2 (4.02 g, 8.36 mmol) and Compound a-2 (6.47 g, 16.72 mmol) were completely dissolved in 240 mL of tetrahydrofuran in a 500-ml round bottom flask under a nitrogen atmosphere, to which a 2M aqueous potassium carbonate solution (120 ml) was added and tetrakis-(triphenylphosphine)palladium (0.58 g, 0.4350 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 340 mL of ethylacetate to prepare Compound 2 (8.79 g, yield: 62%)

MS: $[M+H]^+=842$

Preparation Example 3: Preparation of Compound 3

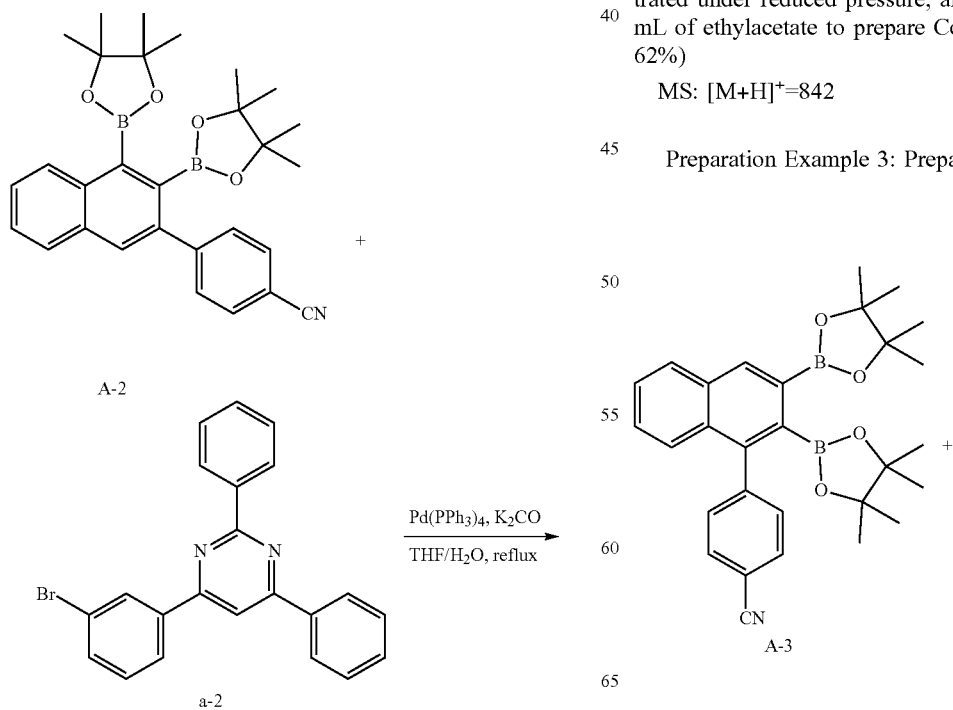

-continued

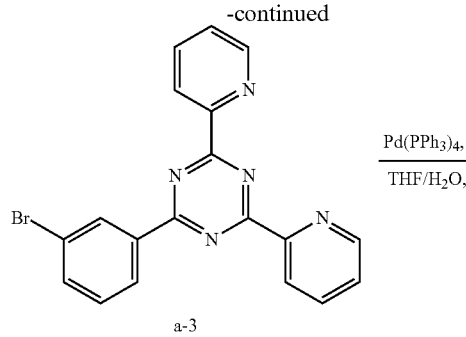

a-3

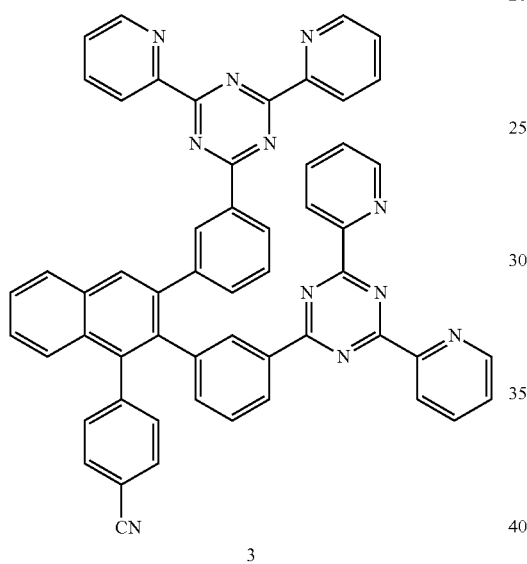

3

Compound A-3 (4.72 g, 9.81 mmol) and Compound a-3 (7.65 g, 19.62 mmol) were completely dissolved in 240 mL of tetrahydrofuran in a 500-ml round bottom flask under a nitrogen atmosphere, to which a 2M aqueous potassium carbonate solution (120 ml) was added and tetrakis-(triphenylphosphine)palladium (0.68 g, 0.59 mmol) was added, and then the resulting mixture was heated and stirred for 7 hours. The temperature was lowered to normal temperature, the aqueous layer was removed, and the resulting product was dried over anhydrous magnesium sulfate, then concentrated under reduced pressure, and recrystallized with 320 mL of tetrahydrofuran to prepare Compound 3 (10.06 g, yield: 60%).

MS: $[M+H]^+=848$

Preparation Example 4: Preparation of Compound 4

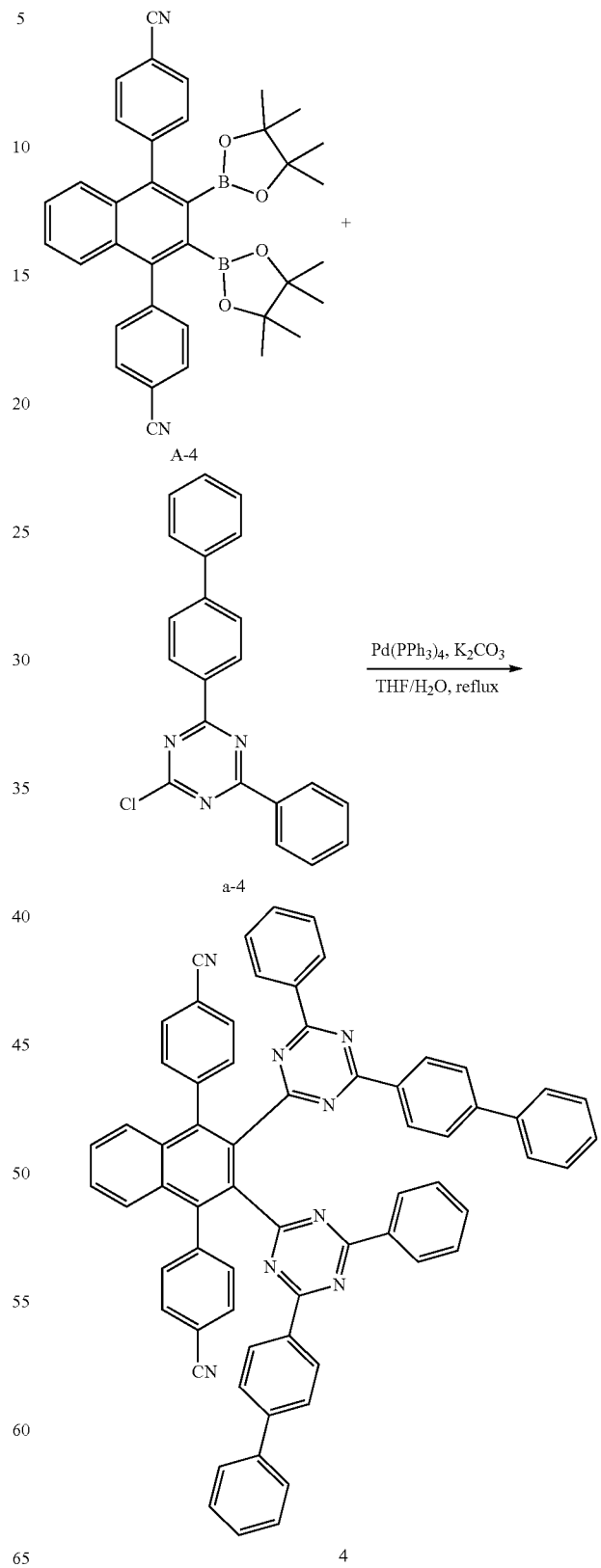

Compound A-4(13.95 g, 23.97 mmol) and Compound a-4 (8.22 g, 23.97 mmol) were completely dissolved in 240 mL of tetrahydrofuran in a 500-ml round bottom flask under a nitrogen atmosphere, to which a 2M aqueous potassium carbonate solution (120 ml) was added and tetrakis-(triphenylphosphine)palladium (0.83 g, 0.72 mmol) was added, and then the resulting mixture was heated and stirred for 6 hours. The temperature was lowered to normal temperature, the aqueous layer was removed, and the resulting product was dried over anhydrous magnesium sulfate, then concentrated under reduced pressure, and recrystallized with 280 mL of toluene to prepare Compound 4 (13.78 g, yield: 61%).
MS: [M+H]⁺=946

Preparation Example 5: Preparation of Compound 5

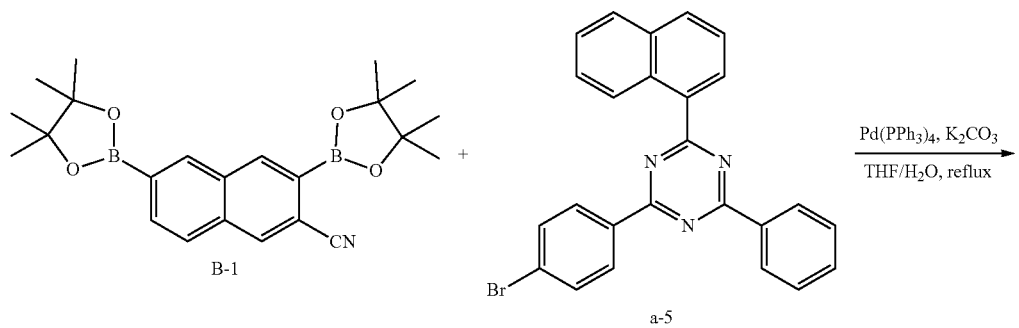

Compound B-1 (3.18 g, 7.86 mmol) and Compound a-5 (6.87 g, 15.72 mmol) were completely dissolved in 240 mL of tetrahydrofuran in a 500-ml round bottom flask under a nitrogen atmosphere, to which a 2M aqueous potassium carbonate solution (120 ml) was added and tetrakis-(triphenylphosphine)palladium (0.55 g, 0.47 mmol) was added, and then the resulting mixture was heated and stirred for 3 hours. The temperature was lowered to normal temperature, the aqueous layer was removed, and the resulting product was dried over anhydrous magnesium sulfate, then concentrated under reduced pressure, and recrystallized with 280 mL of toluene to prepare Compound 5 (9.53 g, yield: 64%).
MS: [M+H]⁺=869

Preparation Example 6: Preparation of Compound 6

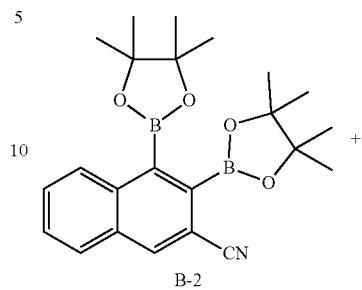

-continued

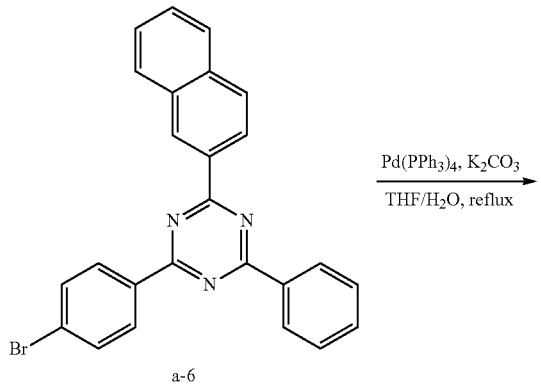

49

-continued

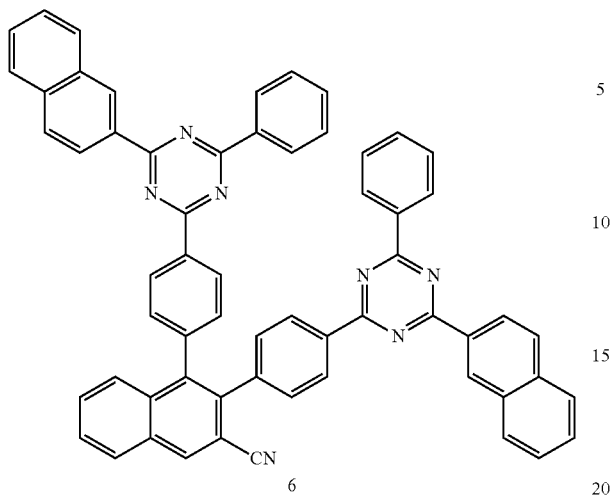

6

Compound B-2 (3.42 g, 8.46 mmol) and Compound a-6 (7.39 g, 16.91 mmol) were completely dissolved in 240 mL of tetrahydrofuran in a 500-ml round bottom flask under a nitrogen atmosphere, to which a 2M aqueous potassium carbonate solution (120 ml) was added and tetrakis-(triphenylphosphine)palladium (0.59 g, 0.51 mmol) was added, and then the resulting mixture was heated and stirred for 4 hours. The temperature was lowered to normal temperature, the aqueous layer was removed, and the resulting product was dried over anhydrous magnesium sulfate, then concentrated under reduced pressure, and recrystallized with 280 mL of toluene to prepare Compound 6 (8.78 g, yield: 61%).

MS: $[M+H]^+$=869

Preparation Example 7: Preparation of Compound 7

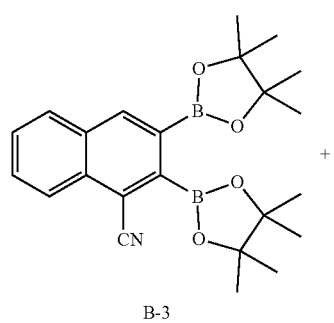

B-3

+

50

-continued

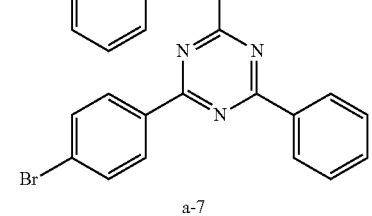

a-7

$\xrightarrow{\text{Pd(PPh}_3)_4, \text{K}_2\text{CO}_3}$
$\text{THF/H}_2\text{O, reflux}$

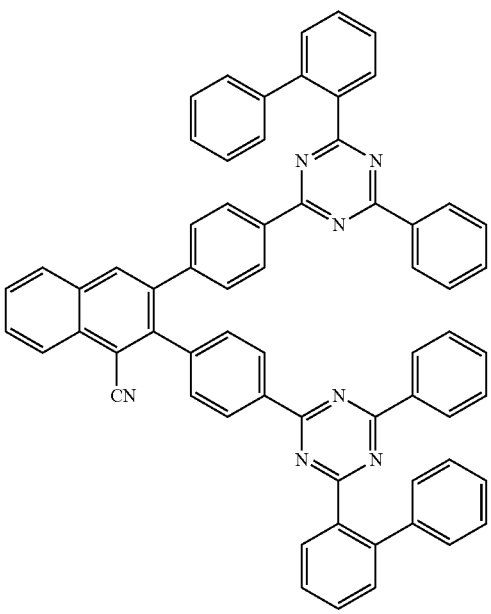

7

Compound B-3 (3.59 g, 8.87 mmol) and Compound a-7 (8.21 g, 17.73 mmol) were completely dissolved in 240 mL of tetrahydrofuran in a 500-ml round bottom flask under a nitrogen atmosphere, to which a 2M aqueous potassium carbonate solution (120 ml) was added and tetrakis-(triphenylphosphine)palladium (0.61 g, 0.53 mmol) was added, and then the resulting mixture was heated and stirred for 3 hours. The temperature was lowered to normal temperature, the aqueous layer was removed, and the resulting product was dried over anhydrous magnesium sulfate, then concentrated under reduced pressure, and recrystallized with 260 mL of toluene to prepare Compound 7 (11.19 g, yield: 69%).

MS: $[M+H]^+$=921

Preparation Example 8: Preparation of Compound 8

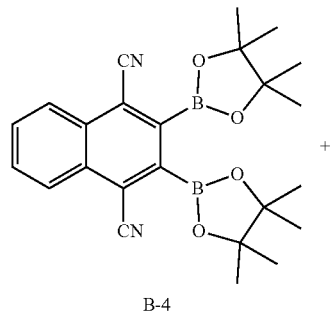

B-4

+

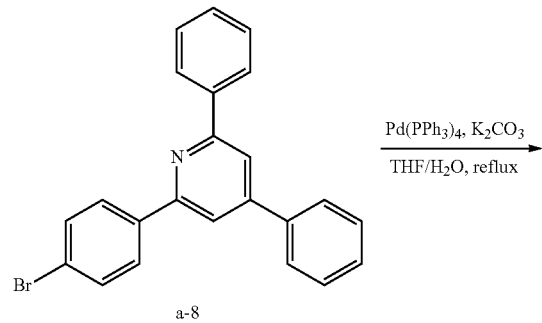

a-8

Pd(PPh$_3$)$_4$, K$_2$CO$_3$
THF/H$_2$O, reflux

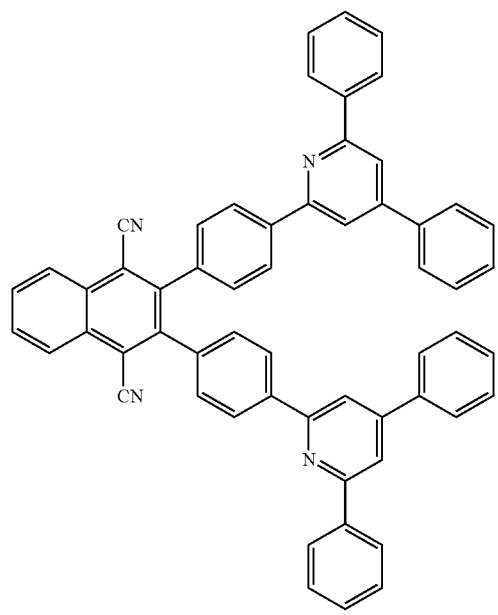

8

Compound B-4 (5.80 g, 13.49 mmol) and Compound a-8 (10.39 g, 26.99 mmol) were completely dissolved in 240 mL of tetrahydrofuran in a 500-ml round bottom flask under a nitrogen atmosphere, to which a 2M aqueous potassium carbonate solution (120 ml) was added and tetrakis-(triphenylphosphine)palladium (0.94 g, 0.81 mmol) was added, and then the resulting mixture was heated and stirred for 3 hours. The temperature was lowered to normal temperature, the aqueous layer was removed, and the resulting product was dried over anhydrous magnesium sulfate, then concentrated under reduced pressure, and recrystallized with 270 mL of toluene to prepare Compound 8 (16.34 g, yield: 77%).

MS: $[M+H]^+$=789

Example 1

A glass substrate on which ITO (indium tin oxide) was coated as a thin film to a thickness of 1000 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma, and then transferred to a vacuum depositor.

On the ITO transparent electrode which is the anode electrode thus prepared, the following compound HI1 and the following compound HI2 were thermally vacuum deposited at a ratio of 98:2 (molar ratio) to have a thickness of 100 Å, thereby forming a hole injection layer. The following compound HT1 (1150 Å) was vacuum deposited on the hole injection layer to form a hole transport layer. The following compound EB1 was vacuum deposited on the hole transport layer to a thickness of 50 Å to form an electron inhibition layer. Then, the following compound BH and the following compound BD were vacuum deposited at a weight ratio of 25:1 on the electron inhibition layer to a thickness of 200 Å to form a light emitting layer. Compound 1 prepared in Preparation Example 1 above was vacuum deposited on the light emitting layer to a thickness of 50 Å to form a hole blocking layer. Then, the following compound ET1 and the following compound LiQ were vacuum deposited at a weight ratio of 1:1 on the hole blocking layer to form an electron injection and transport layer with a thickness of 310 Å. Lithium fluoride (LiF) and aluminum were sequentially deposited to have a thickness of 12 Å and 1000 Å, respectively, on the electron injection and transport layer, thereby forming a cathode.

HI1
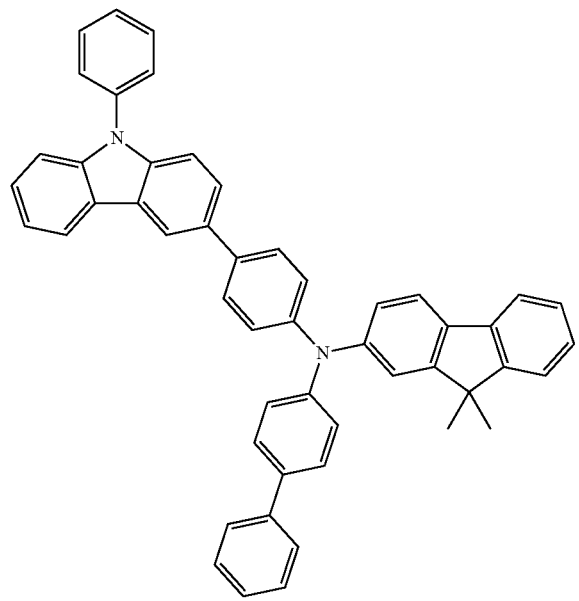
HI2
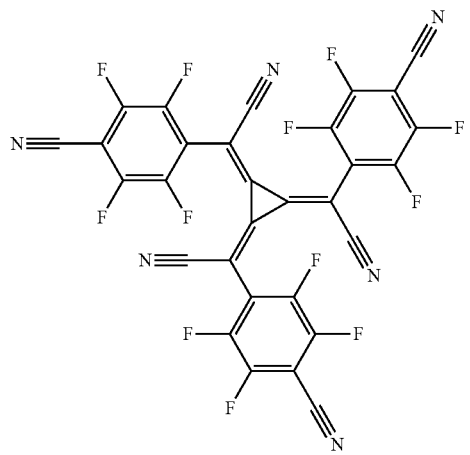
HT1
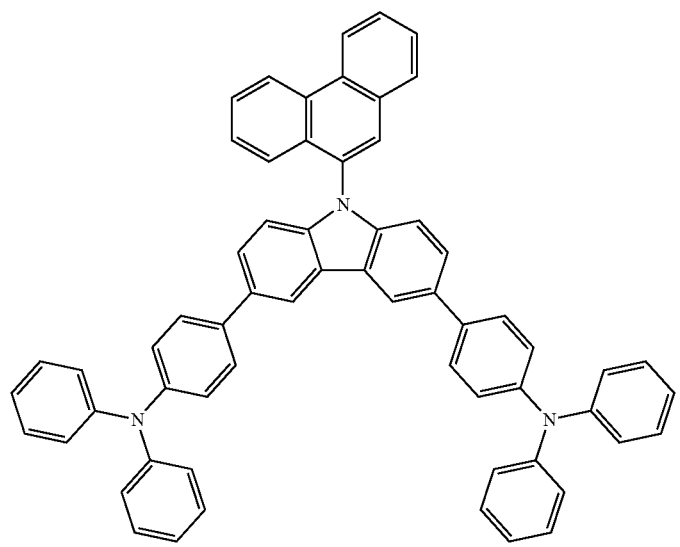
EB1
BH
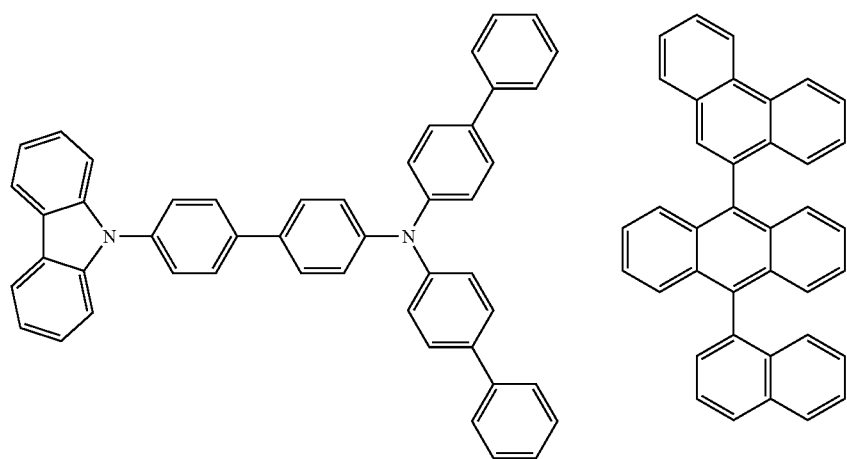

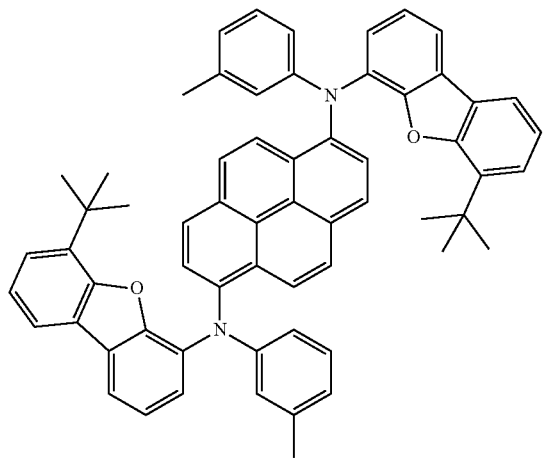

BD

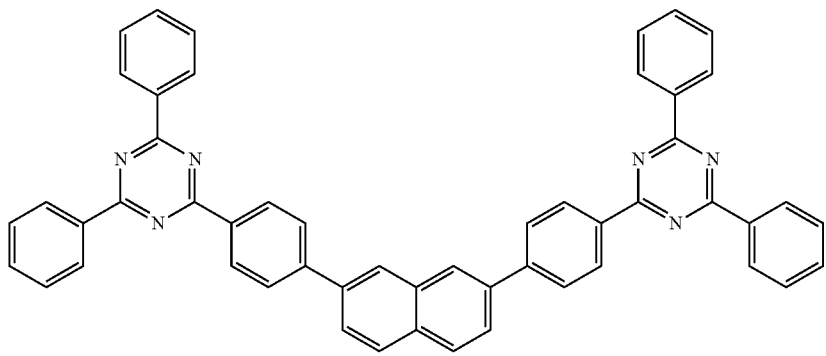

ET1

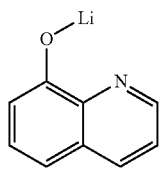

LiQ

In the above-mentioned process, the vapor deposition rate of the organic material was maintained at 0.4 to 0.7 Å/s, the deposition rate of lithium fluoride of the cathode was maintained at 0.3 Å/s, the deposition rate of aluminum was maintained at 2 Å/s, and the degree of vacuum during the deposition was maintained at $2 \times 10^{-7}$ to $5 \times 10^{-6}$ torr, thereby manufacturing an organic light emitting device.

Examples 2 to 8

An organic light emitting device was manufactured in the same manner as in Example 1, except that the compounds shown in Table 1 below were used instead of Compound 1 of Preparation Example 1.

Comparative Examples 1 to 3

An organic light emitting device was manufactured in the same manner as in Example 1, except that the compounds shown in Table 1 below were used instead of Compound 1 of Preparation Example 1. The compounds of HB2, HB3, and HB4 used in Table 1 below are as follows.

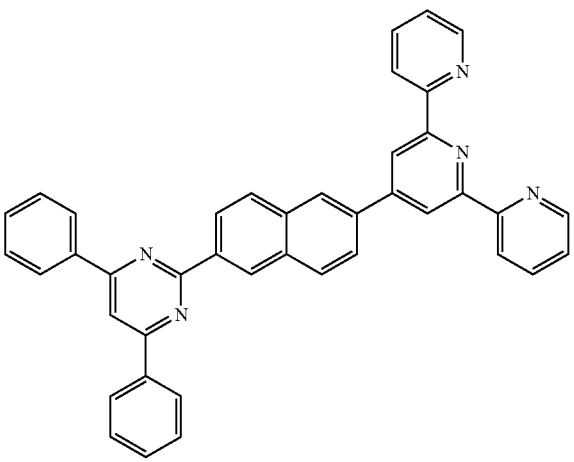

HB2

-continued

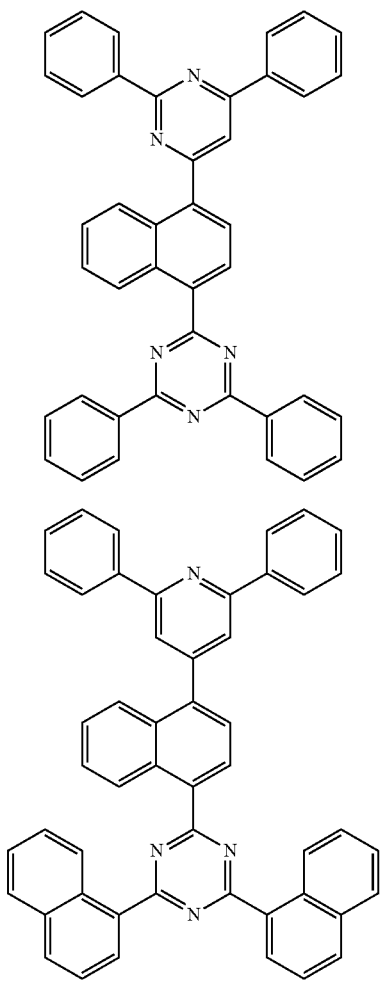

HB3

HB4

Experimental Example

The voltage, efficiency, color coordinates, and lifetime were measured by applying a current of 10 mA/cm² to the organic light emitting devices manufactured in examples and comparative examples, and the results are shown in Table 1 below. T95 means the time required for the luminance to be reduced to 95% of the initial luminance (1600 nit).

TABLE 1

|  | Compound (hole blocking layer) | Voltage (V@10 mA/cm²) | Efficiency (Cd/A@10 mA/cm²) | Color coordinates (x, y) | T95 (h) |
| --- | --- | --- | --- | --- | --- |
| Example 1 | Compound 1 | 4.41 | 6.52 | (0.145, 0.042) | 290 |
| Example 2 | Compound 2 | 4.43 | 6.53 | (0.147, 0.045) | 285 |
| Example 3 | Compound 3 | 4.46 | 6.51 | (0.146, 0.046) | 270 |
| Example 4 | Compound 4 | 4.68 | 6.15 | (0.145, 0.045) | 255 |
| Example 5 | Compound 5 | 4.58 | 6.37 | (0.145, 0.043) | 260 |
| Example 6 | Compound 6 | 4.57 | 6.36 | (0.146, 0.045) | 255 |
| Example 7 | Compound 7 | 4.59 | 6.30 | (0.147, 0.046) | 265 |
| Example 8 | Compound 8 | 4.67 | 6.13 | (0.147, 0.047) | 255 |
| Comparative Example 1 | Compound HB2 | 5.25 | 5.82 | (0.145, 0.046) | 150 |
| Comparative Example 2 | Compound HB3 | 5.08 | 5.73 | (0.144, 0.046) | 165 |
| Comparative Example 3 | Compound HB4 | 5.15 | 5.61 | (0.145, 0.047) | 180 |

As shown in Table 1, the organic light emitting device manufactured by using the compound of the present invention as the hole blocking layer exhibited excellent characteristics in terms of efficiency, driving voltage, and stability of the organic light emitting device.

In Examples 1 to 8, an organic light emitting device manufactured by using a compound of the present invention having one or two cyano substituents connected to naphthylene directly or via a linker and simultaneously containing two triazine substituents exhibited low voltage, high efficiency, and long lifetime characteristics as compared with the organic light emitting devices of Comparative Examples 1, 2, and 3 manufactured by using the compounds HB2, HB3, and HB4 having no cyano substituent

EXPLANATION OF SIGNS

1: substrate 2: anode
3: light emitting layer 4: cathode
5: hole injection layer
6: hole transport layer
7: electron inhibition layer
8: hole blocking layer
9: electron injection and transport layer

The invention claimed is:
1. A compound of Chemical Formula 1:

Chemical Formula 1

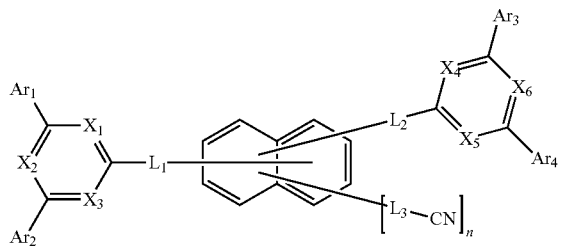

wherein, in Chemical Formula 1:
$X_1$ to $X_3$ are each independently N or CH, provided that at least one of $X_1$ to $X_3$ is N;
$X_4$ to $X_6$ are each independently N or CH, provided that at least one of $X_4$ to $X_6$ is N;
$Ar_1$ to $Ar_4$ are each independently a substituted or unsubstituted $C_{6-60}$ aryl or a substituted or unsubstituted $C_{2-60}$ heteroaryl containing any one or more selected from the group consisting of N, O, and S;
$L_1$ to $L_3$ are each independently a single bond a substituted or unsubstituted $C_{6-60}$ arylene or a substituted or unsubstituted $C_{2-60}$ heteroarylene containing any one or more selected from the group consisting of N, O, and S; and
n is 1 or 2.

2. The compound according to claim 1, wherein Chemical Formula 1 is any one of the following Chemical Formula 1-1 to Chemical Formula 1-5:

Chemical Formula 1-1

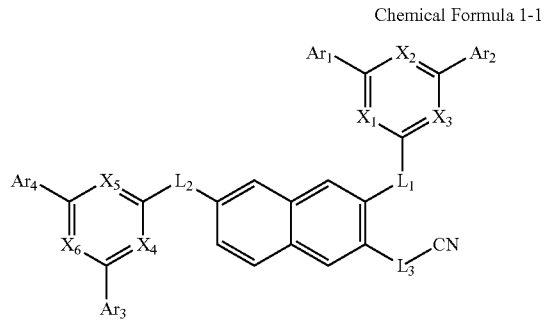

Chemical Formula 1-2

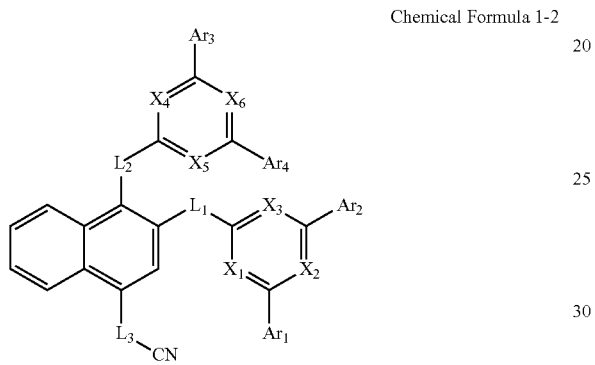

Chemical Formula 1-3

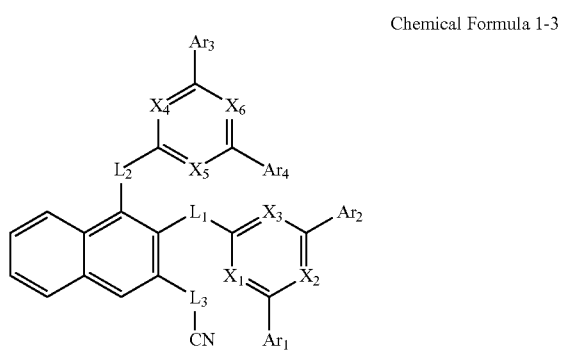

Chemical Formula 1-4

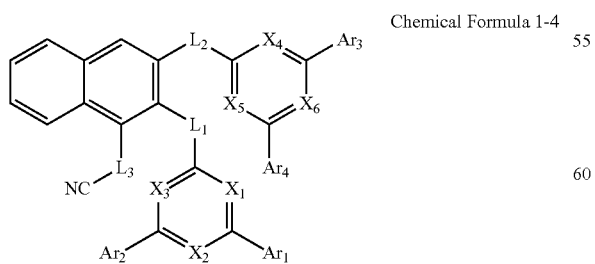

Chemical Formula 1-5

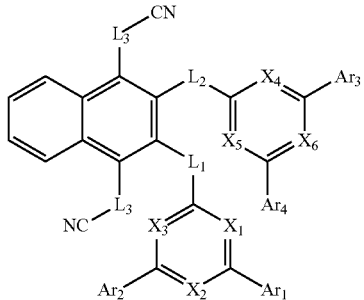

wherein, in Chemical Formulas 1-1 to 1-5, $X_1$ to $X_6$, $Ar_1$ to $Ar_4$, and $L_1$ to $L_3$ are the same as those defined in claim 1.

3. The compound according to claim 1, wherein $Ar_1$ to $Ar_4$ are each independently phenyl, pyridinyl, biphenylyl, terphenylyl, naphthyl, or phenanthrenyl.

4. The compound according to claim 1, wherein $Ar_1$ and $Ar_3$ are the same as each other, and $Ar_2$ and $Ar_4$ are the same as each other.

5. The compound according to claim 1, wherein $L_1$ to $L_3$ are each independently a single bond, phenylene, biphenylylene, terphenylene, or naphthylene.

6. The compound according to claim 1, wherein at least one of $L_1$ to $L_3$ is phenylene.

7. The compound according to claim 1, wherein the compound of Chemical Formula 1 is any one compound selected from the group consisting of the following compounds:

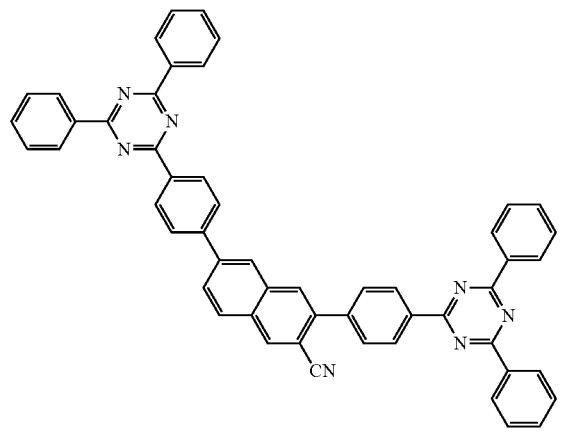

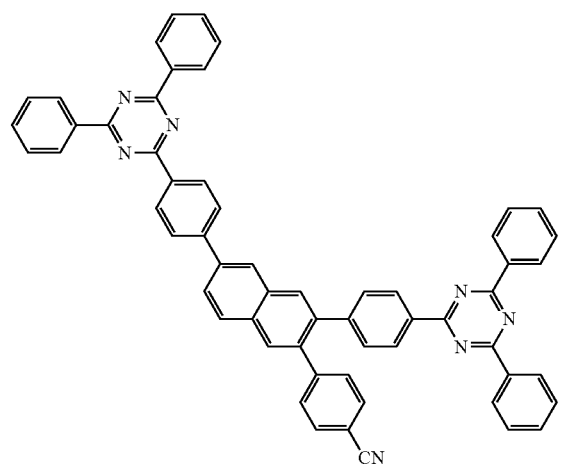
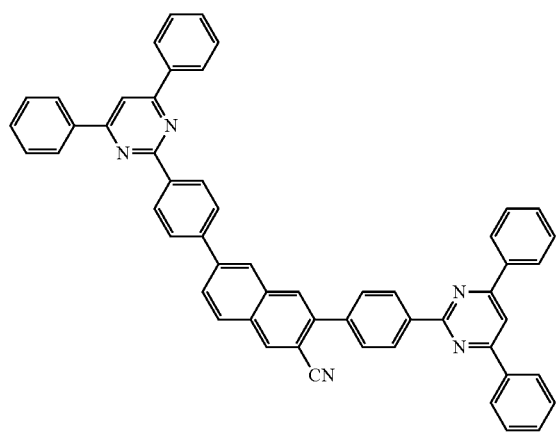
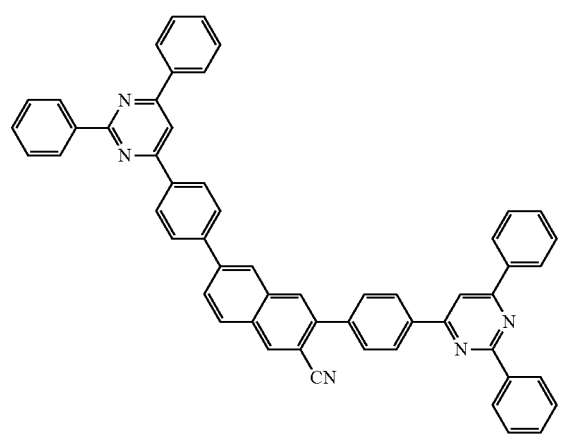
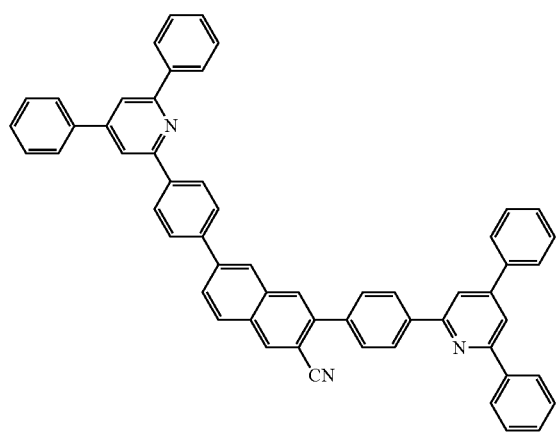

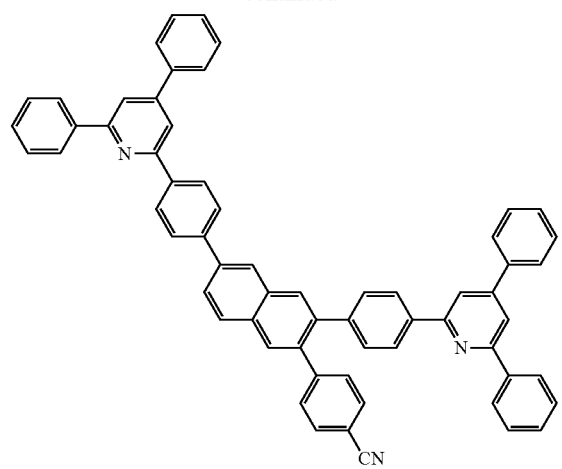
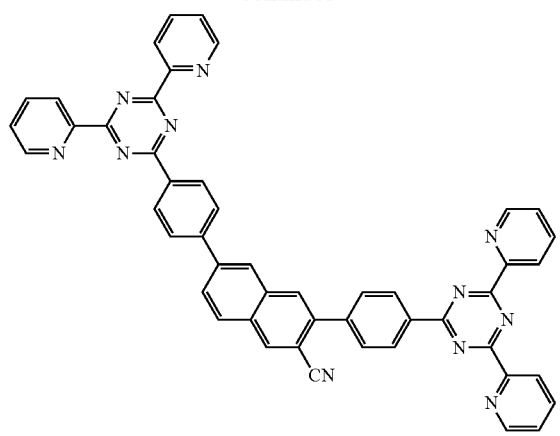
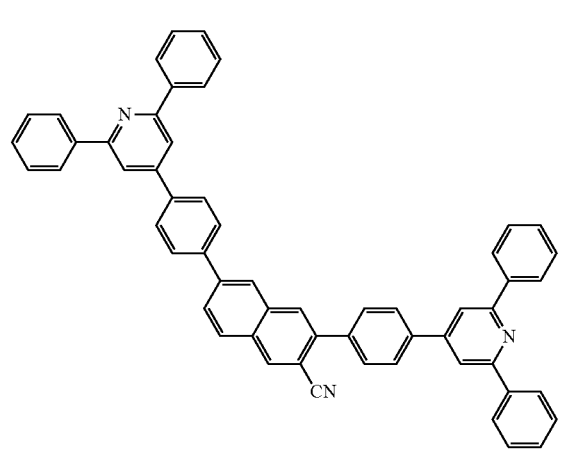
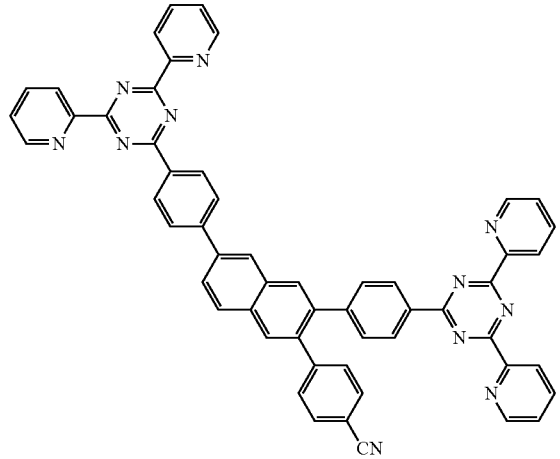
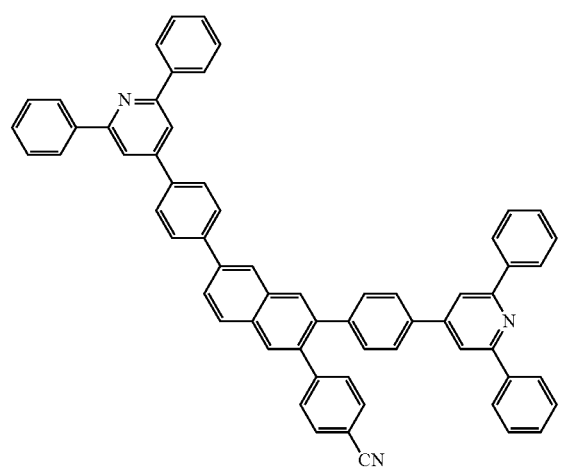

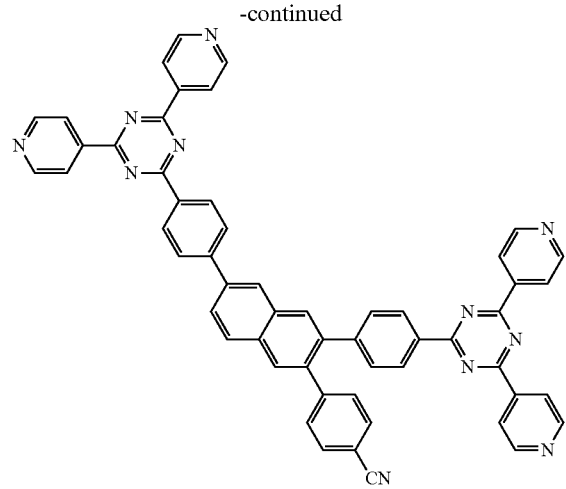
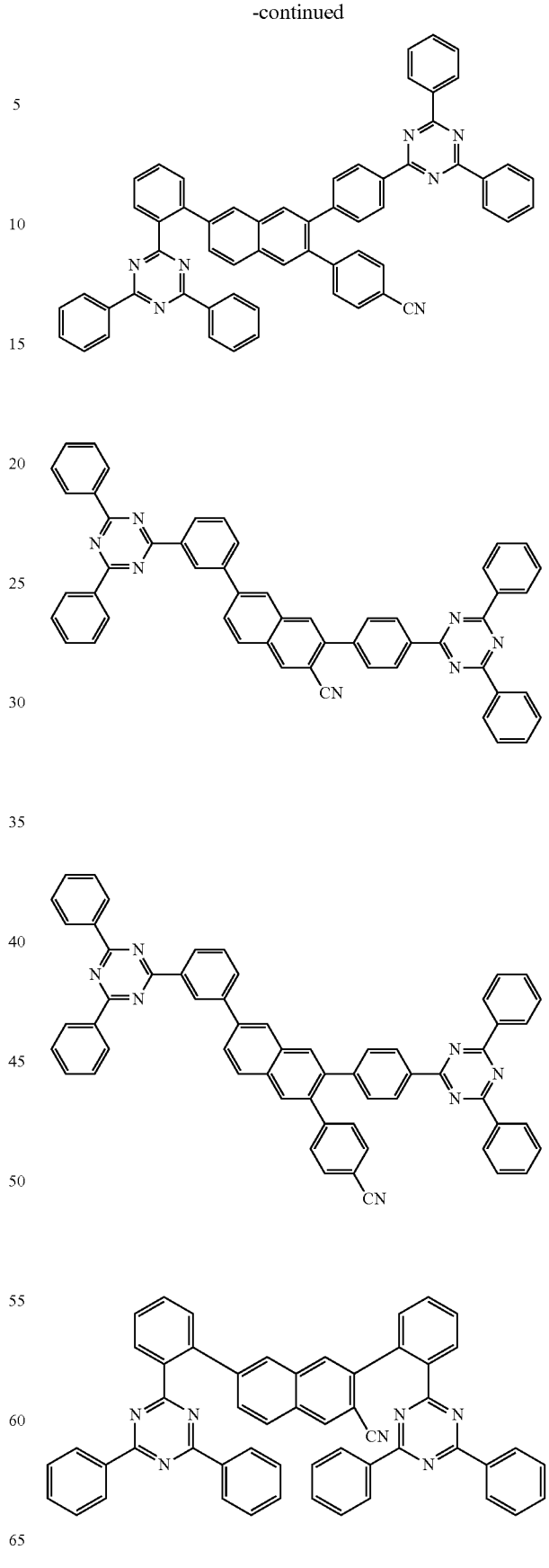

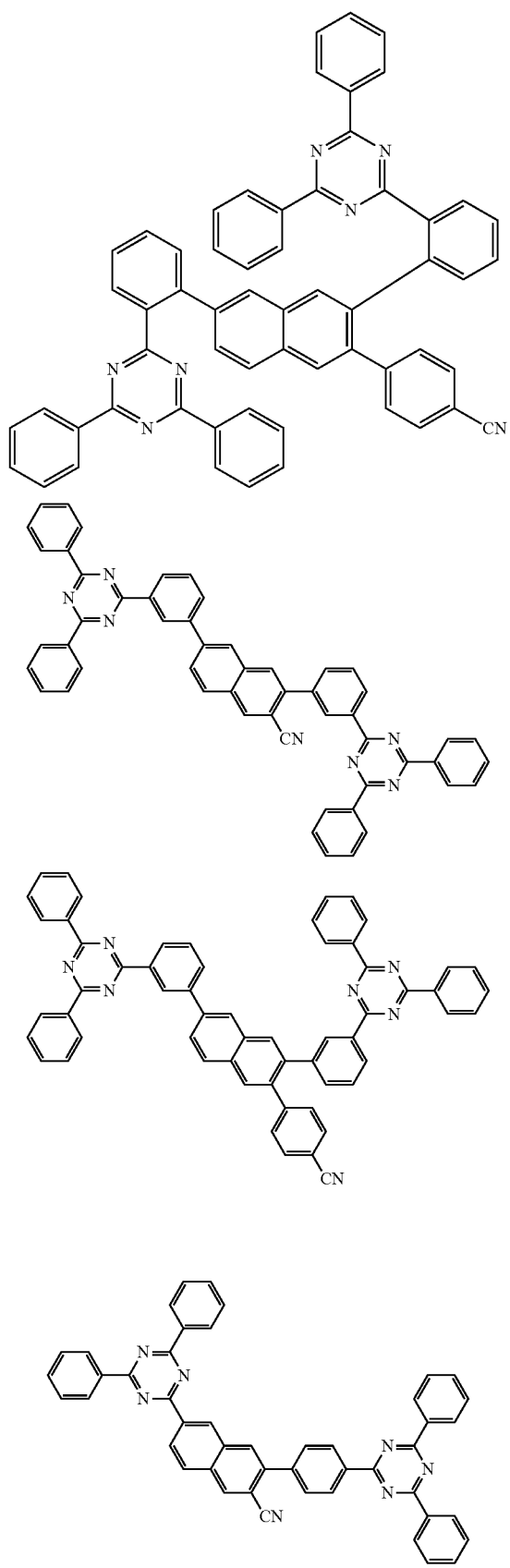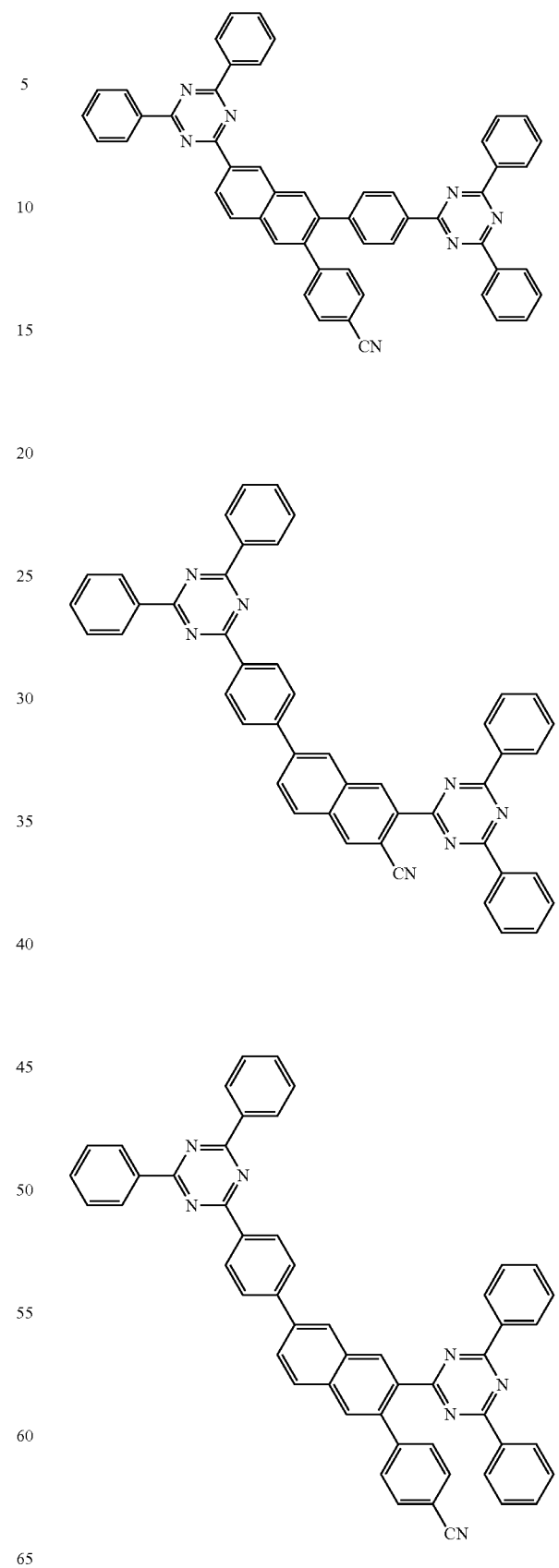

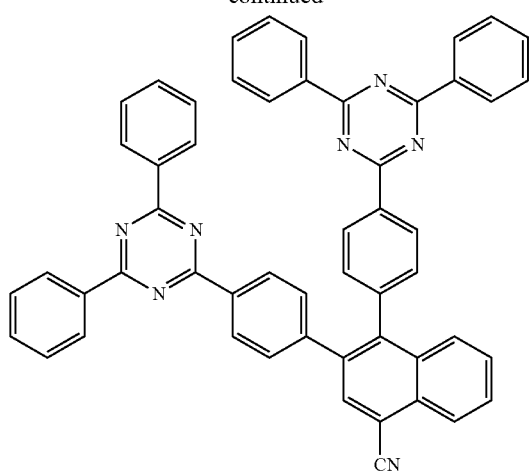
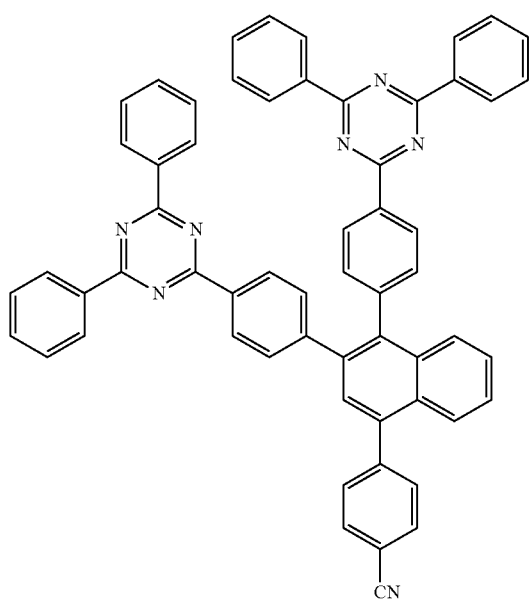
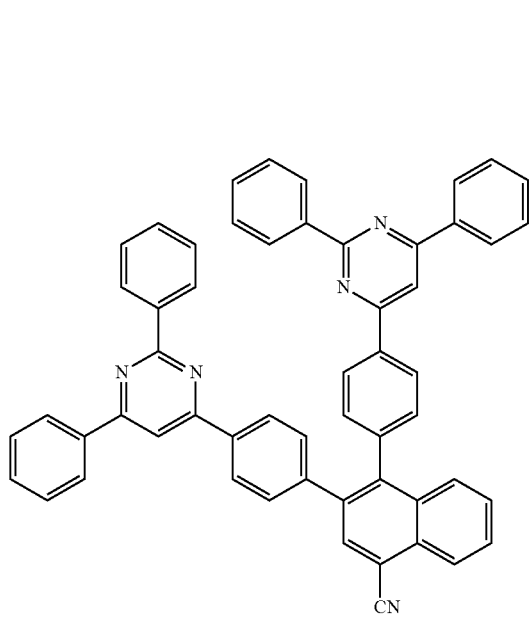
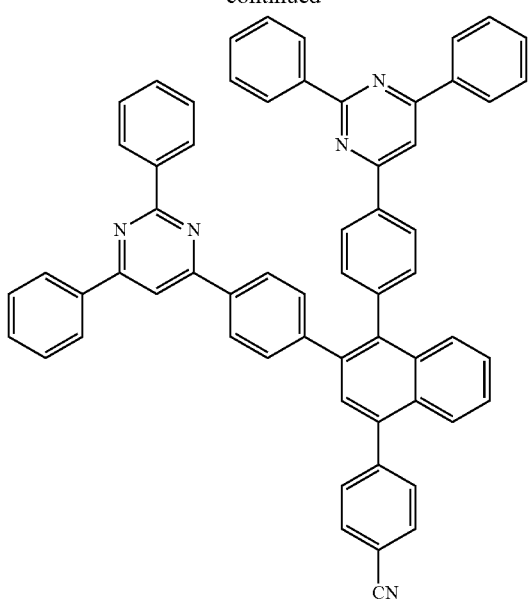
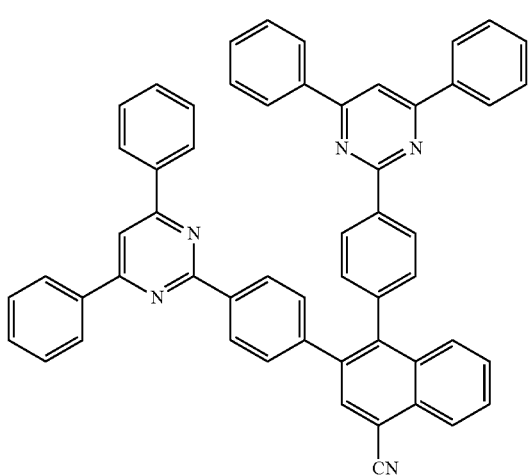
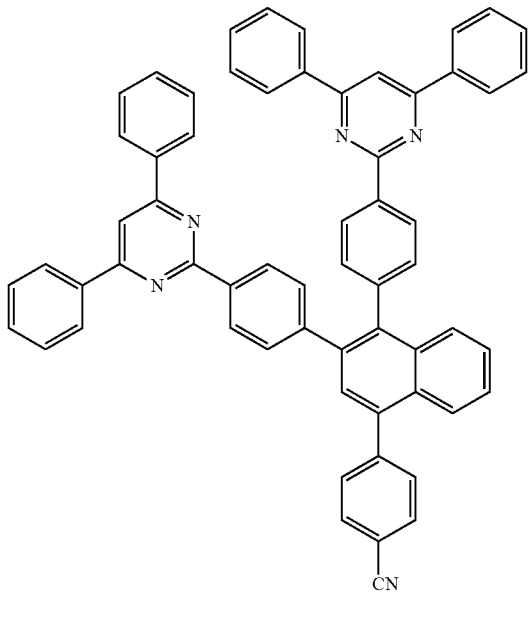

71
-continued
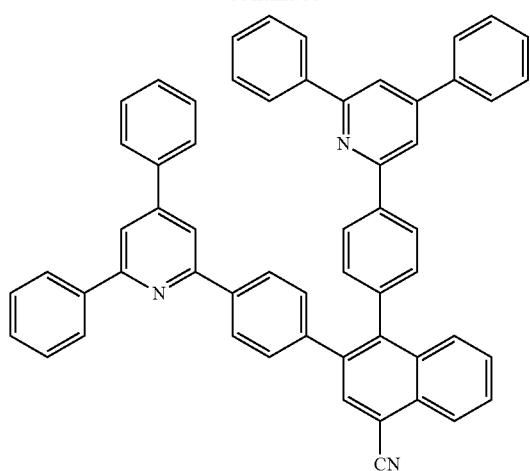
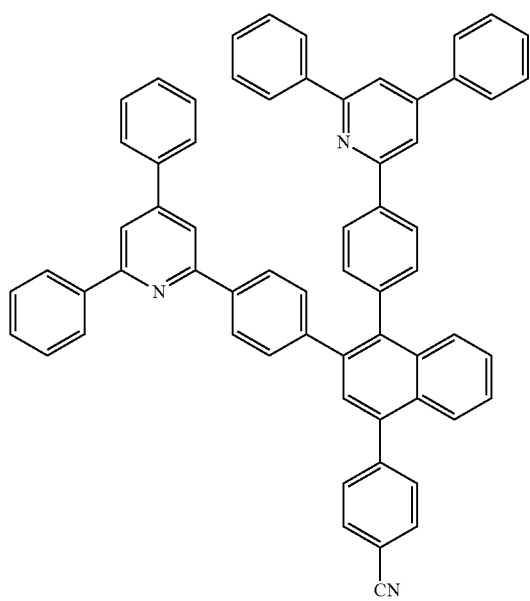
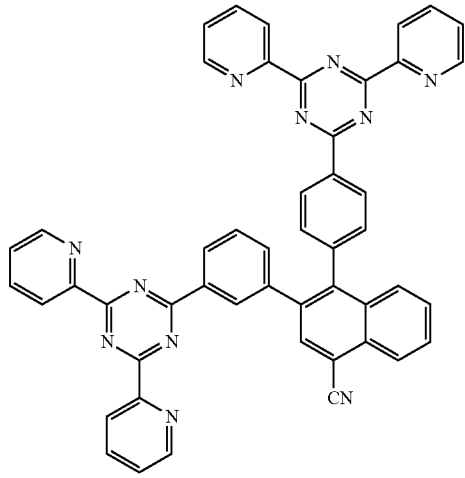
72
-continued
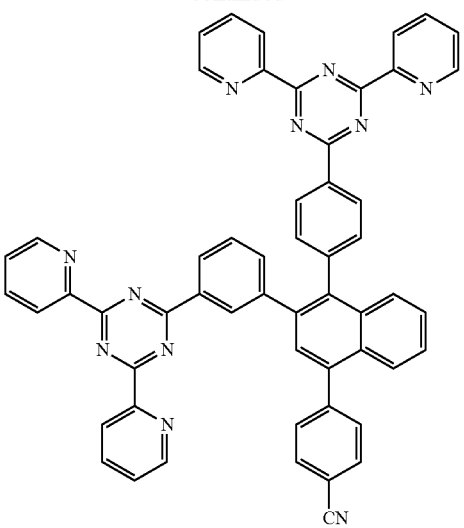
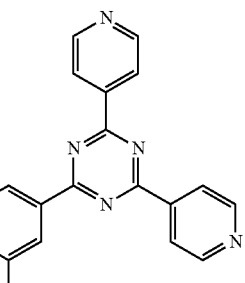
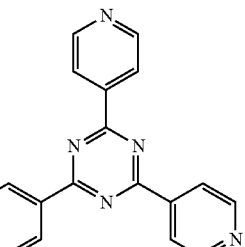
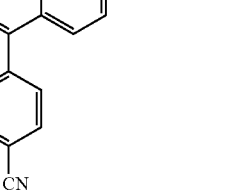

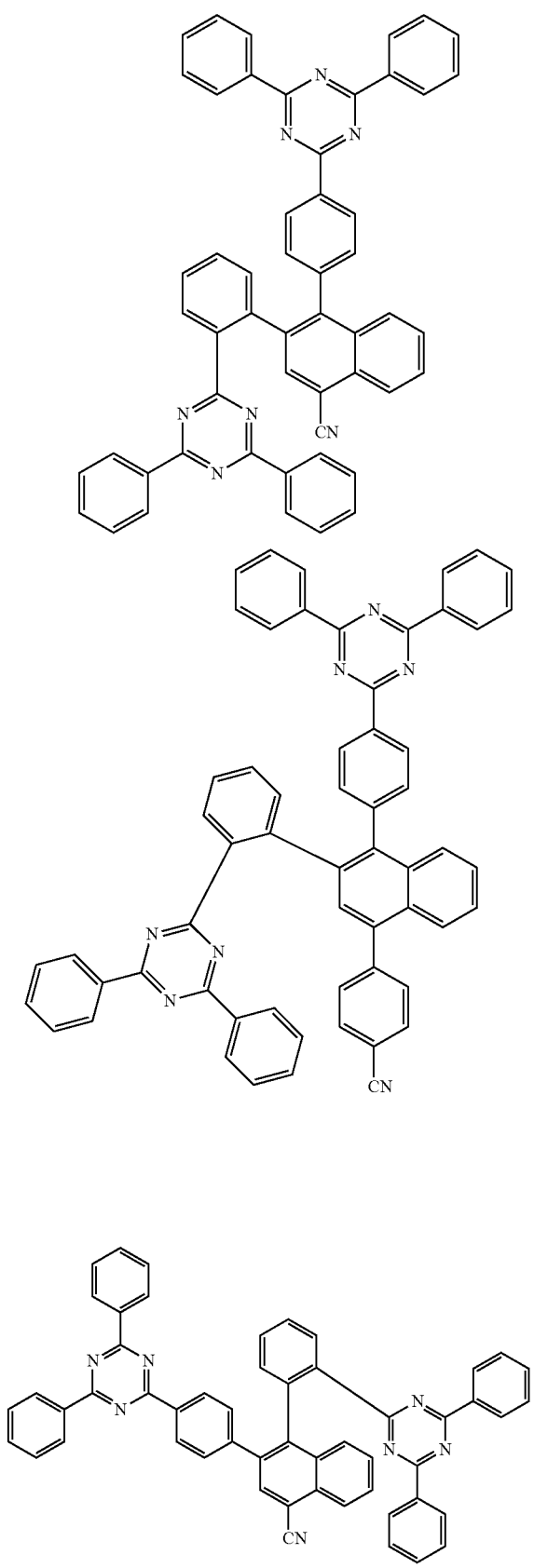
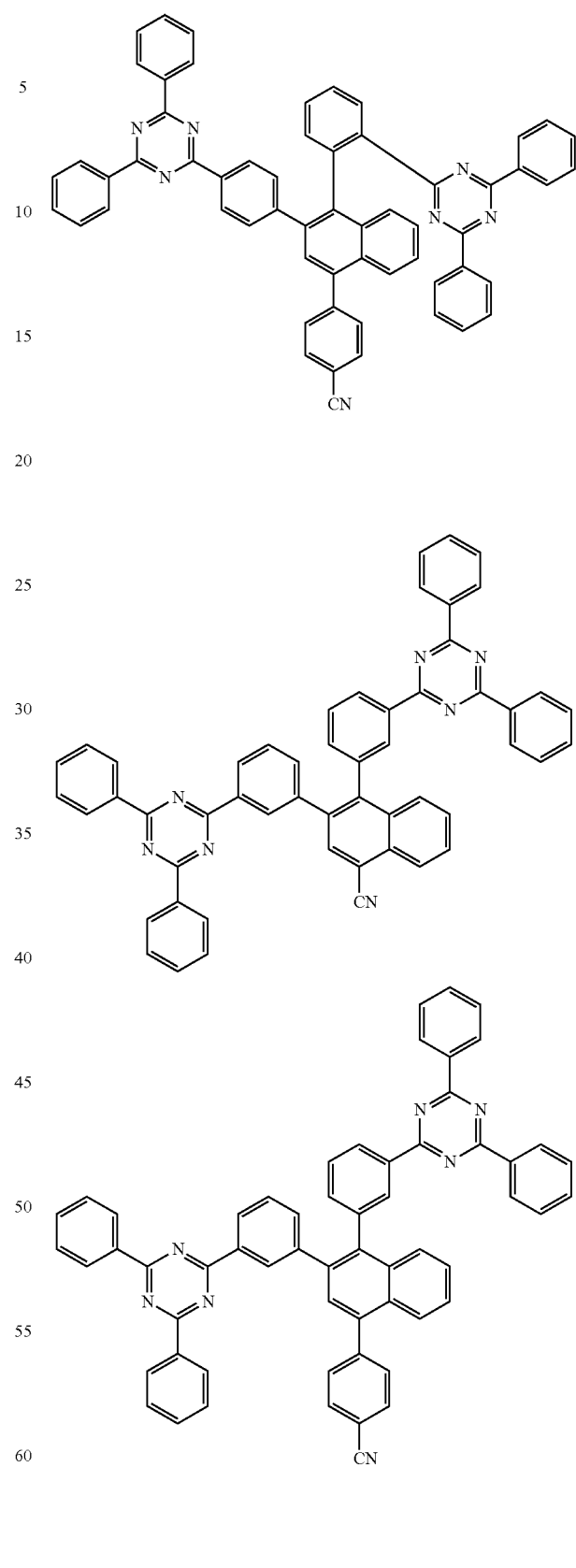

75
-continued
76
-continued
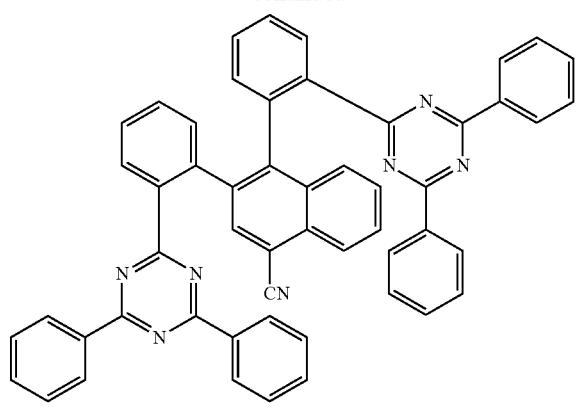
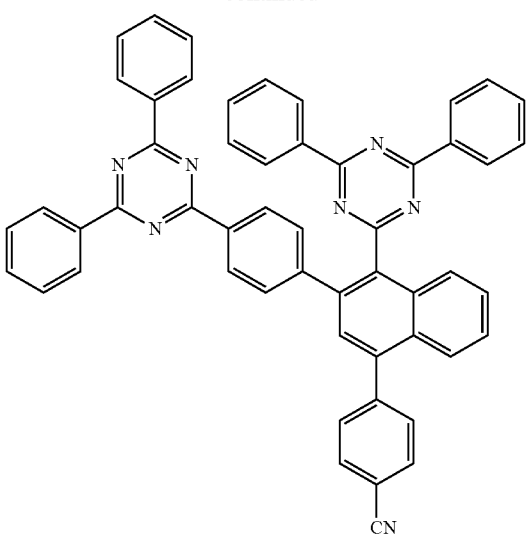

77
-continued
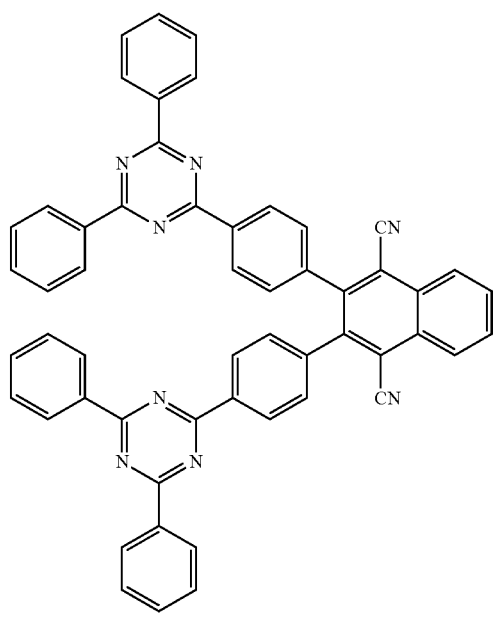
78
-continued
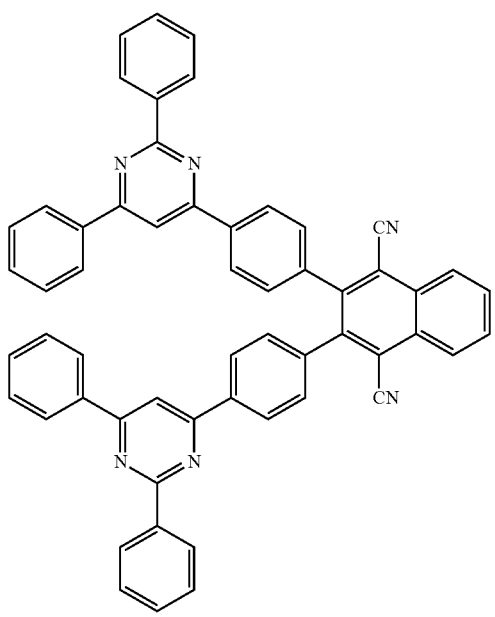
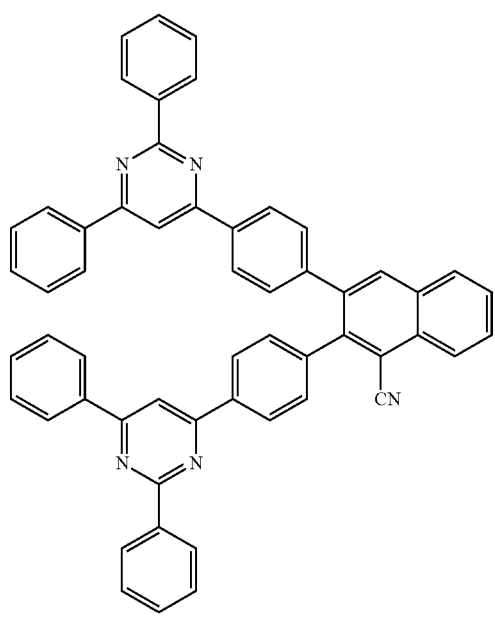
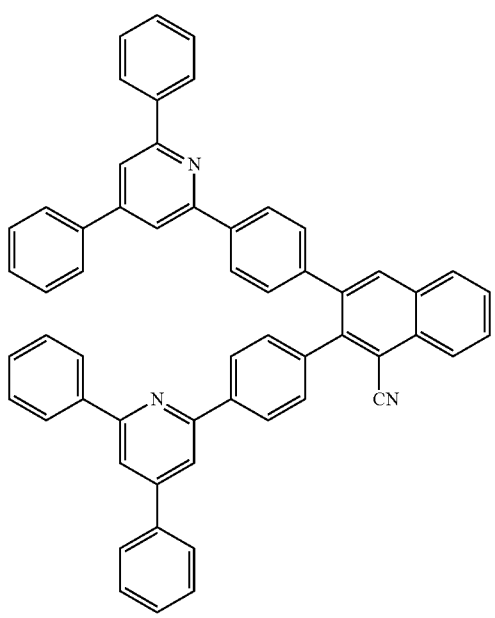

79
-continued
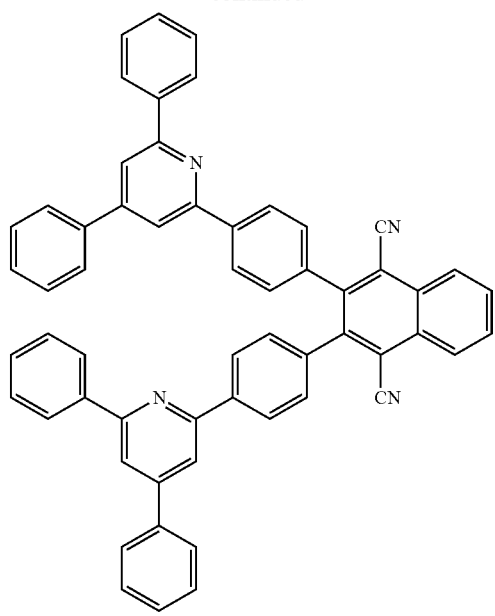
80
-continued
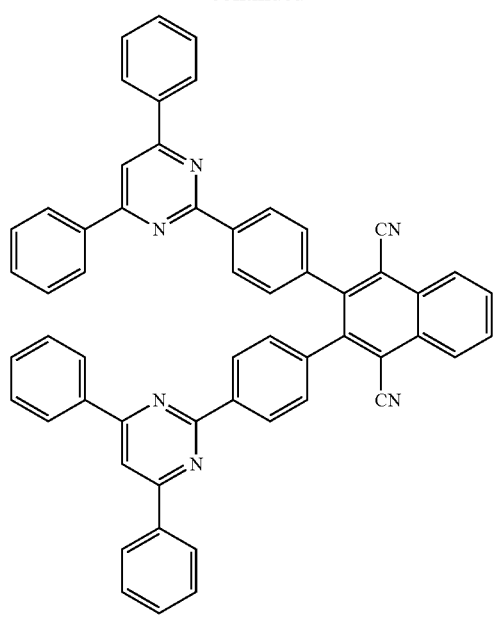
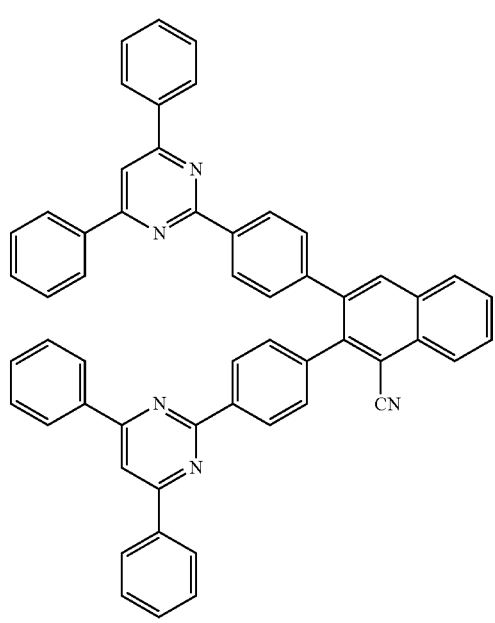
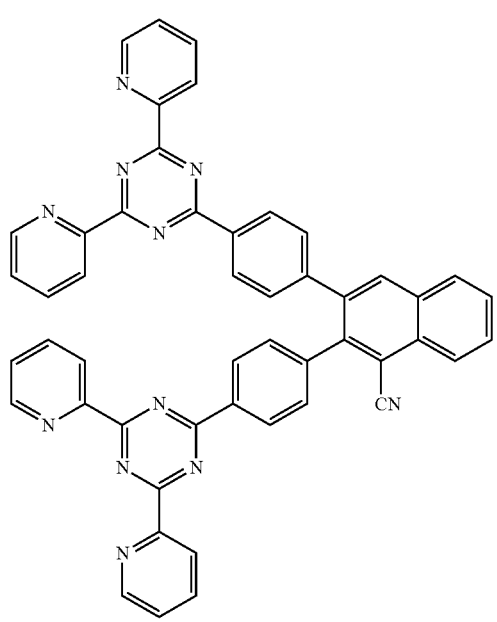

81
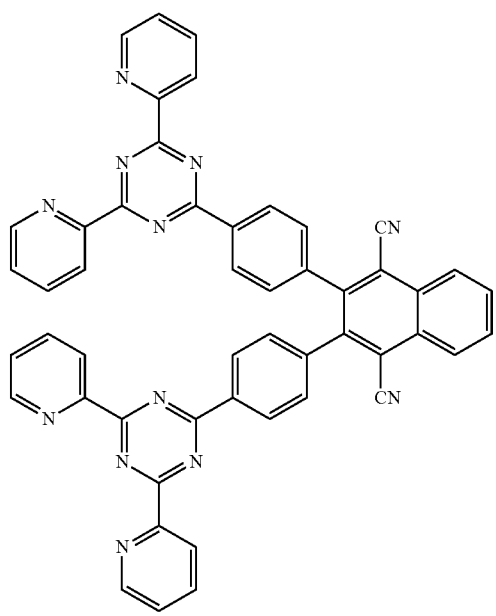
82
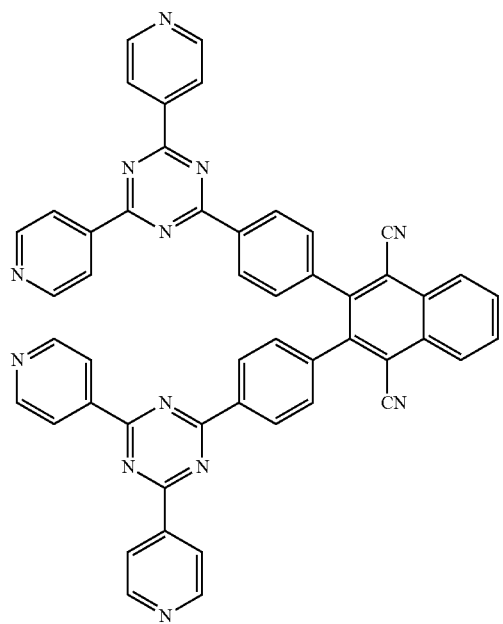
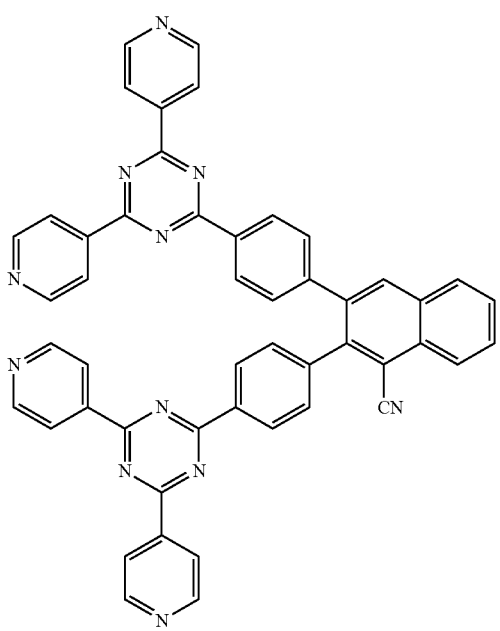

83
-continued
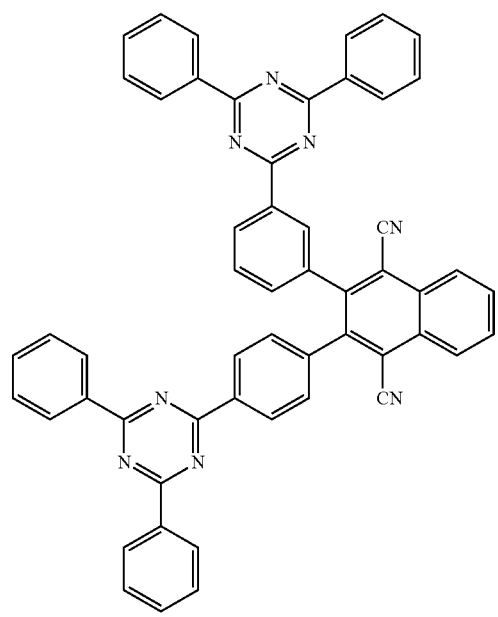
84
-continued
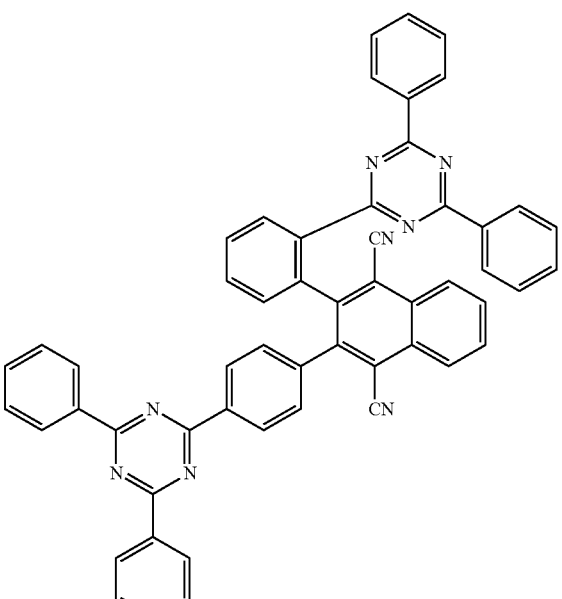
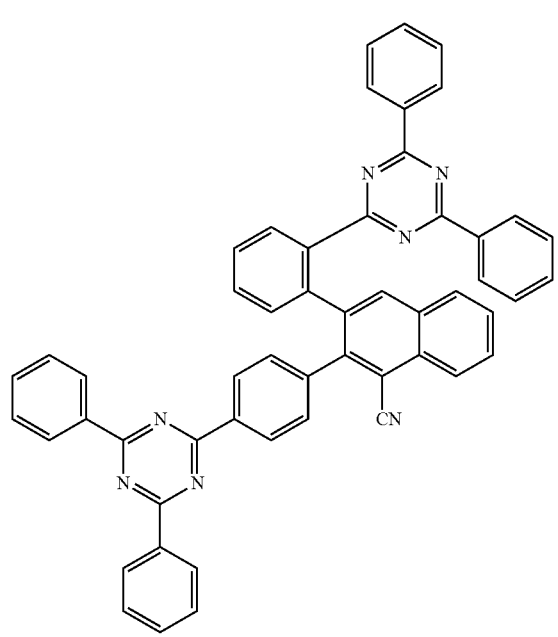
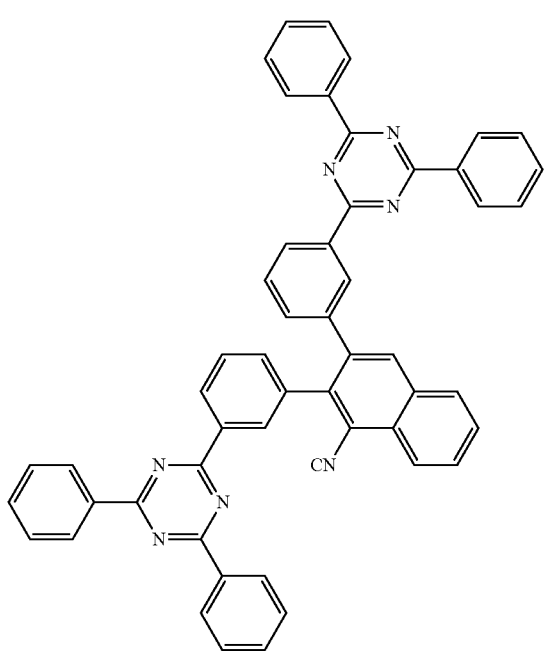

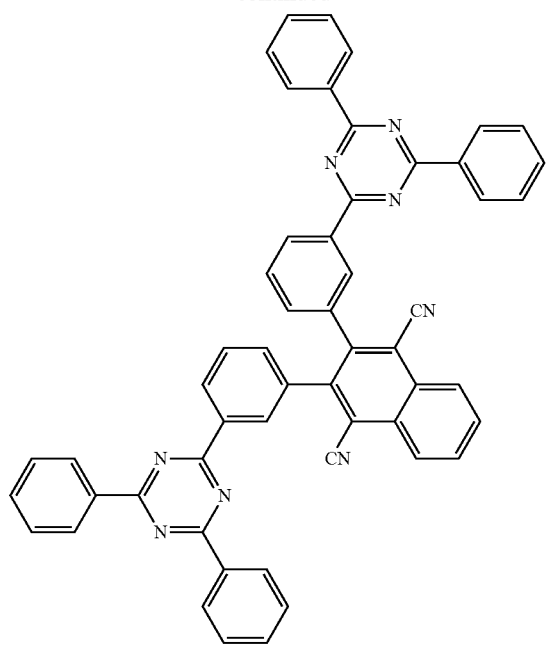
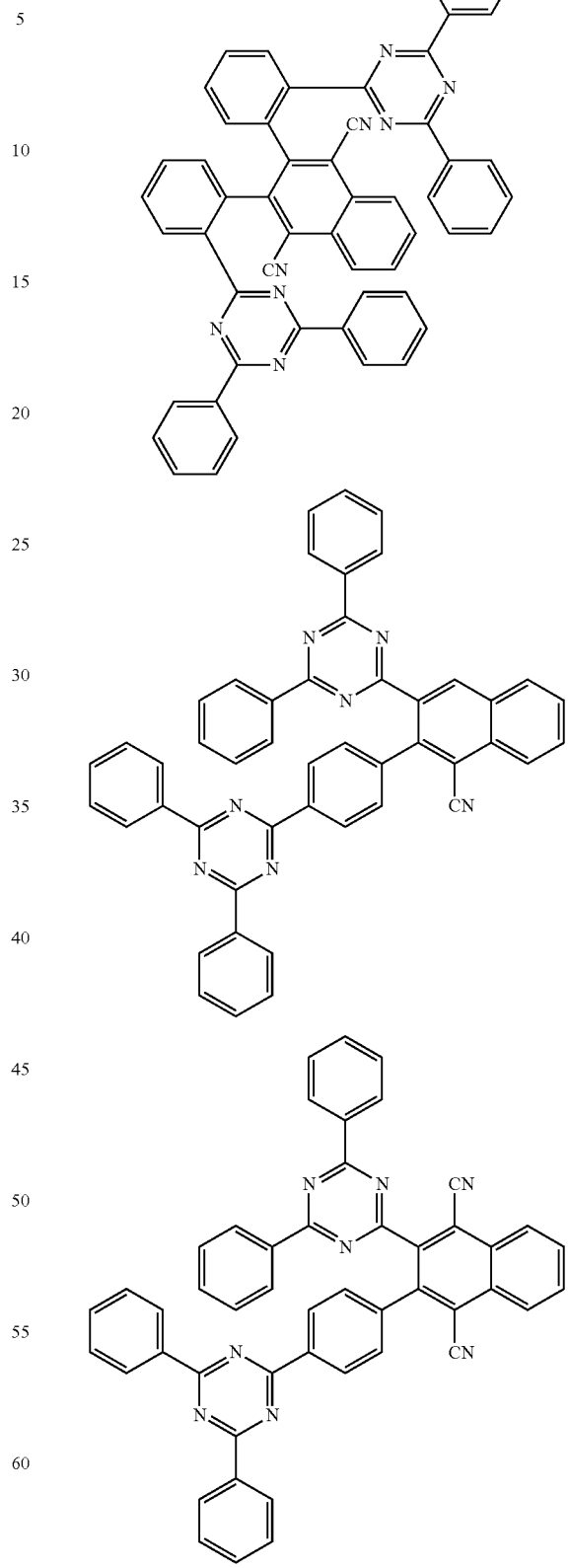

87
-continued
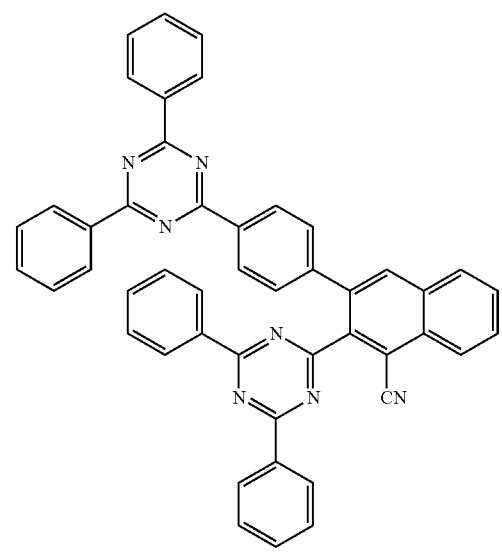
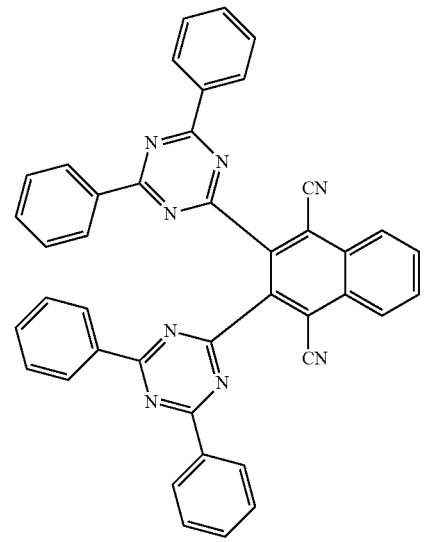
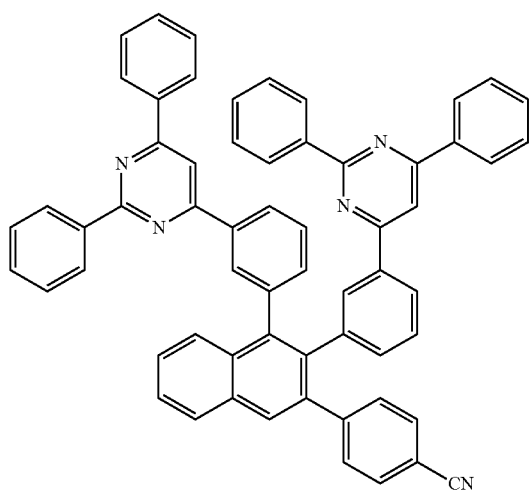
88
-continued
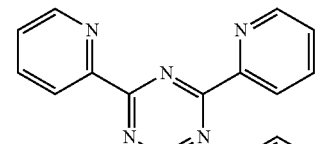
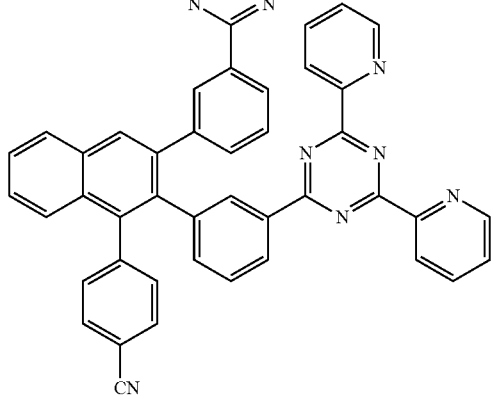
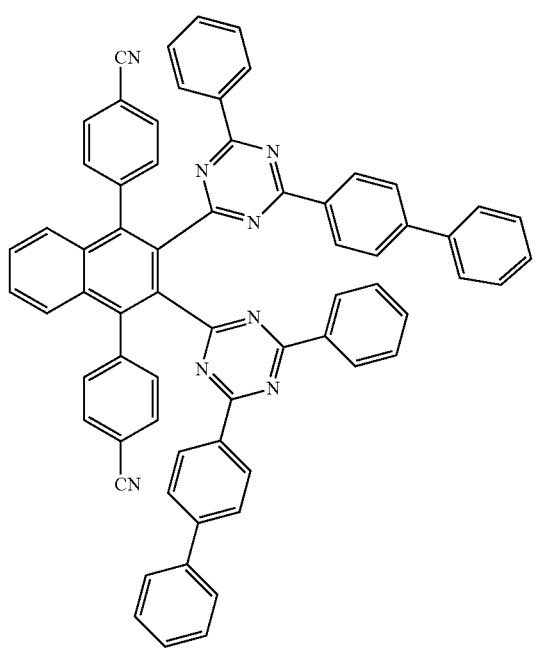
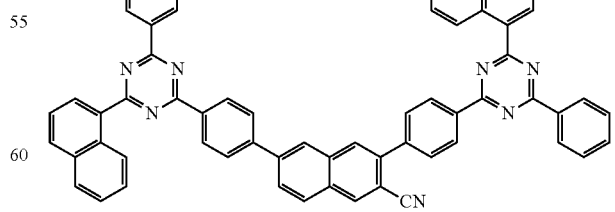

-continued

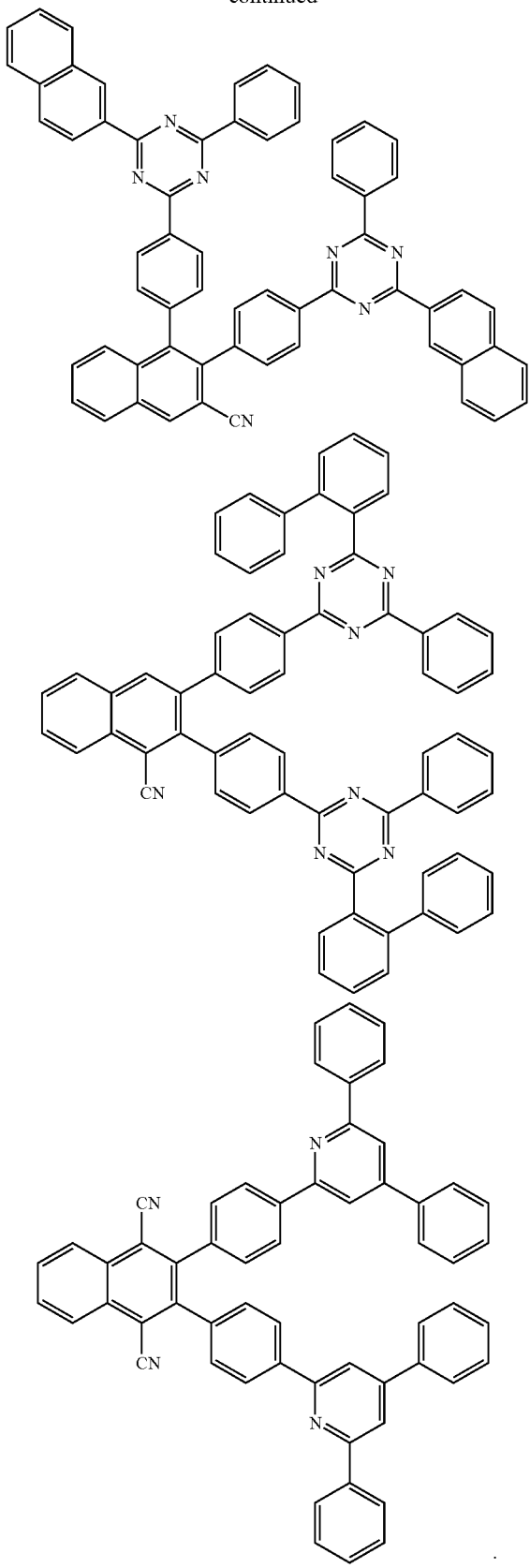

8. An organic light emitting device, comprising:
a first electrode;
a second electrode provided to face the first electrode; and
one or more organic material layers provided between the first electrode and the second electrode,
wherein one or more layers of the organic material layers comprise the compound of claim 1.

9. The organic light emitting device according to claim 8, wherein the organic material layer including the compound is: an electron injection layer; an electron transport layer; a layer for simultaneously performing electron injection and electron transport; or a hole blocking layer.

10. An organic light emitting device, comprising:
a first electrode;
a second electrode provided to face the first electrode; and
one or more organic material layers provided between the first electrode and the second electrode,
wherein one or more one layers of the organic material layers comprise the compound of claim 2.

11. An organic light emitting device, comprising:
a first electrode;
a second electrode provided to face the first electrode; and
one or more organic material layers provided between the first electrode and the second electrode,
wherein one or more one layers of the organic material layers comprise the compound of claim 3.

12. An organic light emitting device, comprising:
a first electrode;
a second electrode provided to face the first electrode; and
one or more organic material layers provided between the first electrode and the second electrode,
wherein one or more one layers of the organic material layers comprise the compound of claim 4.

13. An organic light emittting device, comprising:
a first electrode;
a second electrode provided to face the first electrode; and
one or more organic material layers provided between the first electrode and the second electrode,
wherein one or more one layers of the organic material layers comprise the compound of claim 5.

14. An organic light emitting device, comprising:
a first electrode;
a second electrode provided to face the first electrode; and
one or more organic material layers provided between the first electrode and the second electrode,
wherein one or more one layers of the organic material layers comprise the compound of claim 6.

15. An organic light emitting device, comprising:
a first electrode;
a second electrode provided to face the first electrode; and
one or more organic material layers provided between the first electrode and the second electrode,
wherein one or more one layers of the organic material layers comprise the compound of claim 7.

* * * * *